(12) United States Patent
Kovacs et al.

(10) Patent No.: US 10,390,772 B1
(45) Date of Patent: Aug. 27, 2019

(54) SCALE-BASED ON-DEMAND CARE SYSTEM

(71) Applicant: Physiowave, Inc., Santa Clara, CA (US)

(72) Inventors: Gregory T. Kovacs, Palo Alto, CA (US); Richard M. Wiard, Campbell, CA (US)

(73) Assignee: Physiowave, Inc., Menlo Park, CA (US)

( * ) Notice: Subject to any disclaimer, the term of this patent is extended or adjusted under 35 U.S.C. 154(b) by 0 days.

(21) Appl. No.: 15/587,090

(22) Filed: May 4, 2017

Related U.S. Application Data

(60) Provisional application No. 62/331,655, filed on May 4, 2016.

(51) Int. Cl.
| | |
|---|---|
| *A61B 5/0205* | (2006.01) |
| *A61B 5/02* | (2006.01) |
| *G01G 19/44* | (2006.01) |
| *A61B 5/00* | (2006.01) |

(52) U.S. Cl.
CPC .......... *A61B 5/7465* (2013.01); *A61B 5/0004* (2013.01); *A61B 5/0022* (2013.01); *A61B 5/0205* (2013.01); *A61B 5/486* (2013.01); *A61B 5/4833* (2013.01); *A61B 5/7225* (2013.01); *A61B 5/7246* (2013.01); *A61B 5/7275* (2013.01); *G01G 19/44* (2013.01)

(58) Field of Classification Search
CPC ... A61B 5/7465; A61B 5/0004; A61B 5/0022; A61B 5/0205; A61B 5/4833; A61B 5/486; A61B 5/7225; A61B 5/7246; A61B 5/7275; G01G 19/44; G01G 19/50; G01G 19/52; G01G 23/36; G01G 23/37; G01G 23/3707; G01G 23/3728; G01G 23/3735; G01G 23/3742; G01G 19/4146
See application file for complete search history.

(56) References Cited

U.S. PATENT DOCUMENTS

| | | |
|---|---|---|
| 3,702,113 A | 11/1972 | Blockley et al. |
| 4,195,643 A | 4/1980 | Pratt, Jr. |
| 4,362,164 A | 12/1982 | Little et al. |
| 4,557,271 A | 12/1985 | Stoller et al. |
| 4,657,025 A | 4/1987 | Orlando |
| 4,679,569 A | 7/1987 | Lee |
| 4,765,321 A | 8/1988 | Mohri |

(Continued)

*Primary Examiner* — Randy W Gibson
(74) *Attorney, Agent, or Firm* — Crawford Maunu PLLC

(57) ABSTRACT

Certain aspects of the disclosure are directed to an on-demand healthcare apparatus used to enrich the doctor-patient relationship, provide accessible specialized care, while also reducing costs. The apparatus includes a weighing scale including a platform and processing circuitry. The processing circuitry or a portion thereof is electrically integrated with a plurality of sensors under the platform and collects physiological data from the user while the user is standing on the platform. The processing circuitry aggregates scale-obtained data with user data from a plurality of user devices and/or medical devices, filters a database or a system of computer networks with the aggregated data in response to the aggregated data matching trigger data indicating the user is at risk for a health condition, and provides the aggregated data and filtered data to external circuitry accessible by a healthcare professional for review and for providing on-demand care.

21 Claims, 10 Drawing Sheets

(56) References Cited

U.S. PATENT DOCUMENTS

| | | |
|---|---|---|
| 4,836,215 A | 6/1989 | Lee |
| 4,898,182 A | 2/1990 | Hawkins et al. |
| 4,947,857 A | 8/1990 | Albert et al. |
| 4,958,638 A | 9/1990 | Sharpe et al. |
| 5,314,389 A | 5/1994 | Dotan |
| 5,431,170 A | 7/1995 | Mathews |
| 5,620,003 A | 4/1997 | Sepponen |
| 5,678,562 A | 10/1997 | Sellers |
| 5,682,902 A | 11/1997 | Herleikson |
| 5,701,894 A | 12/1997 | Cherry et al. |
| 5,750,937 A | 5/1998 | Johnson et al. |
| 5,782,238 A | 7/1998 | Beitler |
| 5,833,623 A | 11/1998 | Mann et al. |
| 6,038,465 A * | 3/2000 | Melton, Jr. .......... A61B 5/1171 600/407 |
| 6,047,203 A | 4/2000 | Sackner et al. |
| 6,080,110 A | 6/2000 | Thorgersen |
| 6,168,563 B1 | 1/2001 | Brown |
| 6,198,394 B1 | 3/2001 | Jacobsen et al. |
| 6,205,547 B1 | 3/2001 | Davis |
| 6,228,033 B1 | 5/2001 | Koobi et al. |
| 6,256,532 B1 * | 7/2001 | Cha .................... A61B 5/0537 177/245 |
| 6,292,690 B1 | 9/2001 | Petrucelli |
| 6,331,162 B1 | 12/2001 | Mitchell |
| 6,454,708 B1 | 9/2002 | Ferguson et al. |
| 6,454,719 B1 | 9/2002 | Greenhut |
| 6,516,221 B1 | 2/2003 | Hirouchi et al. |
| 6,551,252 B2 | 4/2003 | Sackner et al. |
| 6,594,759 B1 | 7/2003 | Wang |
| 6,640,134 B2 | 10/2003 | Raymond et al. |
| 6,685,634 B1 | 2/2004 | Fry |
| 6,702,754 B2 | 3/2004 | Ogura et al. |
| 6,705,990 B1 | 3/2004 | Gallant |
| 6,734,856 B2 | 5/2004 | Ishikawa et al. |
| 6,755,783 B2 | 6/2004 | Cosentino et al. |
| 6,783,498 B2 | 8/2004 | Sackner et al. |
| 6,790,178 B1 | 9/2004 | Mault et al. |
| 6,814,705 B2 | 11/2004 | Kawaguchi |
| 6,847,892 B2 | 1/2005 | Zhou et al. |
| 6,875,174 B2 | 4/2005 | Braun et al. |
| 6,898,299 B1 | 5/2005 | Brooks |
| 6,962,566 B2 | 11/2005 | Quistgaard et al. |
| 6,963,035 B2 | 11/2005 | Honda et al. |
| 7,137,955 B2 | 11/2006 | Bartels et al. |
| 7,257,438 B2 | 8/2007 | Kinast |
| 7,313,435 B2 | 12/2007 | Nakada et al. |
| 7,316,648 B2 | 1/2008 | Kelly et al. |
| 7,336,266 B2 | 2/2008 | Hayward et al. |
| 7,382,247 B2 | 6/2008 | Welch et al. |
| 7,384,410 B2 | 6/2008 | Eggers et al. |
| 7,417,536 B2 | 8/2008 | Lakshmanan et al. |
| 7,459,644 B2 | 12/2008 | Kenmochi |
| 7,502,643 B2 | 3/2009 | Farringdon et al. |
| 7,593,632 B2 | 9/2009 | Schnell |
| 7,668,588 B2 | 2/2010 | Kovacs |
| 7,787,946 B2 | 8/2010 | Stahmann et al. |
| 7,796,013 B2 | 9/2010 | Murakami et al. |
| 7,846,104 B2 | 12/2010 | MacQuarrie et al. |
| 7,899,522 B1 | 3/2011 | Koh et al. |
| 8,200,320 B2 | 6/2012 | Kovacs |
| 8,332,026 B2 | 12/2012 | Cha et al. |
| 8,369,936 B2 | 2/2013 | Farringdon et al. |
| 8,452,390 B2 | 5/2013 | Jensen |
| 8,473,041 B2 | 6/2013 | Bartnik et al. |
| 8,475,367 B1 | 7/2013 | Yuen et al. |
| 8,475,368 B2 | 7/2013 | Tran et al. |
| 8,529,409 B1 | 9/2013 | Lesea-Ames |
| 8,548,556 B2 | 10/2013 | Jensen |
| 8,639,226 B2 | 1/2014 | Hutchings et al. |
| 8,682,424 B2 | 3/2014 | Tsoglin et al. |
| 8,698,014 B1 | 4/2014 | Walstad |
| 8,858,449 B2 | 10/2014 | Inan et al. |
| 8,870,780 B2 | 10/2014 | Inan et al. |
| 9,011,346 B2 | 4/2015 | Wiard et al. |
| 9,055,871 B2 | 6/2015 | Inan et al. |
| 9,215,991 B2 | 12/2015 | Inan et al. |
| 9,241,637 B2 | 1/2016 | Wiard et al. |
| 2001/0030546 A1 | 10/2001 | Yamada et al. |
| 2001/0044588 A1 | 11/2001 | Mault |
| 2002/0002326 A1 | 1/2002 | Causey, III et al. |
| 2002/0062090 A1 | 5/2002 | Chai et al. |
| 2002/0188205 A1 | 12/2002 | Mills |
| 2003/0050537 A1 | 3/2003 | Wessel |
| 2003/0088196 A1 | 5/2003 | Steve |
| 2003/0126593 A1 | 7/2003 | Mault |
| 2003/0130567 A1 | 7/2003 | Mault et al. |
| 2003/0130595 A1 | 7/2003 | Mault |
| 2003/0149349 A1 | 8/2003 | Jensen |
| 2003/0197614 A1 | 10/2003 | Smith et al. |
| 2003/0233034 A1 | 12/2003 | Varri et al. |
| 2004/0068379 A1 | 4/2004 | Morgan et al. |
| 2004/0073127 A1 | 4/2004 | Istvan et al. |
| 2004/0097802 A1 | 5/2004 | Cohen |
| 2004/0138517 A1 | 7/2004 | Osorio et al. |
| 2004/0211599 A1 | 10/2004 | Kasinoff |
| 2004/0249258 A1 | 12/2004 | Tupin, Jr. et al. |
| 2005/0004483 A1 | 1/2005 | Lin |
| 2005/0017602 A1 | 1/2005 | Arms et al. |
| 2005/0033124 A1 | 2/2005 | Kelly et al. |
| 2005/0043645 A1 | 2/2005 | Ono et al. |
| 2005/0113703 A1 | 5/2005 | Farringdon et al. |
| 2005/0119711 A1 | 6/2005 | Cho et al. |
| 2005/0171451 A1 | 8/2005 | Yeo et al. |
| 2005/0203349 A1 | 9/2005 | Nanikashvili |
| 2005/0206518 A1 | 9/2005 | Welch et al. |
| 2005/0215868 A1 | 9/2005 | Kenjou et al. |
| 2005/0247494 A1 | 11/2005 | Montagnino |
| 2005/0283198 A1 | 12/2005 | Haubrich et al. |
| 2006/0049955 A1 | 3/2006 | Blum et al. |
| 2006/0064030 A1 * | 3/2006 | Cosentino ............ A61B 5/0031 600/547 |
| 2006/0079942 A1 | 4/2006 | Deno et al. |
| 2006/0106646 A1 | 5/2006 | Squilla et al. |
| 2006/0111641 A1 | 5/2006 | Manera et al. |
| 2006/0116589 A1 | 6/2006 | Park |
| 2006/0122525 A1 | 6/2006 | Shusterman |
| 2006/0149139 A1 | 7/2006 | Bonmassar et al. |
| 2006/0154642 A1 | 7/2006 | Scannell |
| 2006/0155589 A1 | 7/2006 | Lane et al. |
| 2007/0055324 A1 | 3/2007 | Thompson et al. |
| 2007/0069887 A1 | 3/2007 | Welch et al. |
| 2007/0161913 A1 | 7/2007 | Farrell et al. |
| 2007/0167286 A1 | 7/2007 | Roes |
| 2007/0197878 A1 | 8/2007 | Shklarski |
| 2007/0208232 A1 | 9/2007 | Kovacs |
| 2007/0208233 A1 | 9/2007 | Kovacs |
| 2007/0287928 A1 | 12/2007 | Kiviniemi et al. |
| 2007/0293770 A1 | 12/2007 | Bour et al. |
| 2008/0027679 A1 | 1/2008 | Shklarski |
| 2008/0073128 A1 | 3/2008 | Umemoto |
| 2008/0154645 A1 | 6/2008 | Takehara |
| 2008/0161700 A1 | 7/2008 | Sachanandani et al. |
| 2008/0183090 A1 | 7/2008 | Farringdon et al. |
| 2008/0194975 A1 | 8/2008 | MacQuarrie et al. |
| 2008/0208009 A1 | 8/2008 | Shklarski |
| 2008/0221404 A1 | 9/2008 | Tso |
| 2008/0246629 A1 | 10/2008 | Tsui et al. |
| 2008/0281222 A1 | 11/2008 | Fukada |
| 2008/0306393 A1 | 12/2008 | Ting et al. |
| 2009/0016582 A1 | 1/2009 | Penn et al. |
| 2009/0024044 A1 | 1/2009 | Virtanen et al. |
| 2009/0071731 A1 * | 3/2009 | Gerster ................ A61B 5/022 177/177 |
| 2009/0102296 A1 | 4/2009 | Greene et al. |
| 2009/0182204 A1 | 7/2009 | Semler et al. |
| 2009/0203972 A1 | 8/2009 | Heneghan et al. |
| 2009/0240194 A1 | 9/2009 | Keimel et al. |
| 2009/0284496 A1 | 11/2009 | Oki |
| 2009/0287933 A1 | 11/2009 | Beckwith et al. |
| 2009/0315733 A1 | 12/2009 | Bischoff |
| 2010/0004715 A1 | 1/2010 | Fahey |
| 2010/0016685 A1 | 1/2010 | Muehlsteff et al. |
| 2010/0094147 A1 | 4/2010 | Inan et al. |

(56) References Cited

U.S. PATENT DOCUMENTS

| | | |
|---|---|---|
| 2010/0174205 A1 | 7/2010 | Wegerif |
| 2010/0210921 A1 | 8/2010 | Park et al. |
| 2010/0262044 A1 | 10/2010 | Siegler |
| 2011/0040352 A1 | 2/2011 | Gerber et al. |
| 2011/0054359 A1 | 3/2011 | Sazonov et al. |
| 2011/0080181 A1 | 4/2011 | Sato et al. |
| 2011/0152695 A1 | 6/2011 | Granqvist et al. |
| 2011/0196617 A1* | 8/2011 | Petrucelli ............... A61B 5/022 702/19 |
| 2011/0240379 A1 | 10/2011 | Forshaw et al. |
| 2011/0245710 A1 | 10/2011 | Jensen |
| 2011/0310005 A1 | 12/2011 | Chen |
| 2012/0003933 A1 | 1/2012 | Baker et al. |
| 2012/0065895 A1 | 3/2012 | Saul |
| 2012/0071792 A1 | 3/2012 | Pfeffer et al. |
| 2012/0123219 A1 | 5/2012 | Georgiev et al. |
| 2012/0165622 A1 | 6/2012 | Rodriguez et al. |
| 2012/0245476 A1 | 9/2012 | Skeri et al. |
| 2012/0266250 A1 | 10/2012 | Uhl |
| 2012/0283587 A1 | 11/2012 | Gosh et al. |
| 2012/0302843 A1 | 11/2012 | Otsubo et al. |
| 2012/0318869 A1 | 12/2012 | Edmonds |
| 2013/0006669 A1 | 1/2013 | Nakamura |
| 2013/0056285 A1 | 3/2013 | Meagher |
| 2013/0113506 A1 | 5/2013 | Poupyrev et al. |
| 2013/0226601 A1 | 8/2013 | Razmi et al. |
| 2013/0289889 A1 | 10/2013 | Yuen et al. |
| 2013/0310700 A1 | 11/2013 | Wiard et al. |
| 2014/0089836 A1 | 3/2014 | Damani et al. |
| 2014/0094707 A1 | 4/2014 | Farringdon et al. |
| 2014/0121540 A1 | 5/2014 | Raskin |
| 2014/0142396 A1 | 5/2014 | Ricks et al. |
| 2014/0142437 A1 | 5/2014 | Inan et al. |
| 2014/0172314 A1 | 6/2014 | Baarman et al. |
| 2014/0182952 A1 | 7/2014 | Yuen et al. |
| 2014/0221849 A1 | 8/2014 | Farringdon et al. |
| 2014/0221850 A1 | 8/2014 | Farringdon et al. |
| 2015/0107910 A1 | 4/2015 | Villard et al. |
| 2015/0112209 A1 | 4/2015 | Blaber et al. |
| 2015/0160068 A1 | 6/2015 | Carreel et al. |
| 2015/0168205 A1 | 6/2015 | Lee |
| 2015/0193497 A1 | 7/2015 | Tallamy et al. |
| 2015/0201844 A1 | 7/2015 | Nakagawa |
| 2015/0289802 A1 | 10/2015 | Thomas et al. |
| 2015/0331491 A1 | 11/2015 | Rumreich |
| 2015/0335291 A1 | 11/2015 | Saadi et al. |
| 2015/0338265 A1 | 11/2015 | Carreel et al. |
| 2016/0015276 A1* | 1/2016 | Strauss ................ A61B 5/0537 600/301 |
| 2016/0029905 A1 | 2/2016 | Kovacs |
| 2016/0116326 A1 | 4/2016 | Sharma |
| 2016/0317043 A1 | 11/2016 | Campo et al. |
| 2017/0188845 A1* | 7/2017 | Banet .................. A61B 5/0205 |
| 2017/0209053 A1* | 7/2017 | Pantelopoulos ... A61B 5/02125 |

\* cited by examiner

SCALE-BASED ON-DEMAND CARE SYSTEM

SUMMARY OF THE DISCLOSURE

Various aspects of the present disclosure are directed toward methods, systems and apparatuses that are useful in a scale-based on-demand care system.

Due to technology changes, including access to smart user devices, consumers are receiving more and more personalized services. For example, in healthcare, consumers are prioritizing accessibility and comfort with respect to delivery of care. Additionally, there is increasing pressure to reduce the cost of healthcare. On-demand healthcare is an avenue that can be used to provide accessible and personalized healthcare services to consumers while potentially decreasing healthcare costs. On-demand healthcare, as used herein, includes or refers to healthcare provided to consumers. The healthcare provided, in specific embodiments, can be at a different location than a traditional physician's office or hospital, such as the user's home or at a temporary or remote clinic. In some specific aspects, the physician and/or other type of healthcare provider is located remotely from the location of the user. Additionally and/or alternatively, a first healthcare provider may be located at a first location (e.g., the location of the user) and a second healthcare provider may be located at a second location.

On-demand healthcare can be used to provide consumers with services in a manner that is convenient, simple, and fast and can allow for providing services that may be otherwise unavailable to consumers or that the consumers would have to travel long distances in order to receive. In this manner, on-demand healthcare can enrich the doctor-patient relationship by making physicians and specialized care more accessible to consumers while also reducing costs. Consumers can be seen by a physician in a virtual appointment using a system that collects user data and without the user having to travel to the physician's office. In some embodiments, the physician or a nurse can provide services by traveling to different locations, and/or diagnosis can be verified by a certified physician in another location. The physician or nurse may not be an expert in a particular condition or disorder and a remote physician can be used to provide the consumer with immediate service. As the care can be provided digitally, consumers can receive feedback on progress with a known treatment or condition, thus increasing the personalized care and improving the doctor-patient relationship.

Aspects of the present disclosure are directed to a scale-based on-demand care system. The scale-based on-demand care system can be a transportable system used to diagnose a user, such as a remote diagnosis. The system includes at least one scale, the Internet, an optional standalone central processing unit (CPU), and one or more user devices and/or medical devices, among other devices. The scale collects user data that may be sensitive to the user, such as cardiogram data and data indicative of disorders and disease, and other user data, such as demographic information and weight, when the user is at a different location than a traditional physician's office or hospital, such as the user's home or at a temporary or remote clinic. For example, the scale may be in communication with the other devices, which can include medical devices that measure additional physiological measurements, such as blood pressure, and blood oxygen levels. The aggregated data may be used to medically assess the user. In some specific aspects, the scale-obtained data is output to external circuitry and reviewed, such as by a nurse or a physician, to determine if the user should visit a physician. Thereby, the system may be used to prevent or mitigate visits to a physician that are not needed, and potentially reduce healthcare costs for the patient and/or insurance company.

In further aspects, the scale acts as a hub for user data from the various user devices, such as cardio-related data, exercise data, and/or food or liquid tracking data, among other data. The scale can include trigger data that triggers a filter of data on the system, including user data and data from the Internet via external circuitry. In various specific embodiments, the system filters the user data for data correlated with the condition and filters the Internet for various data regarding the condition and/or matching the filtered user data. Thereby, the scale-based on-demand care system is used as a medical analytic driver that filters the Internet based on user data related to a condition and trigger data and provides the data to a healthcare professional for diagnosis, treatment, and/or to reduce time spent, and thus, reduce healthcare costs.

In other specific aspects, the scale is located in the user's home or other personal location. User data may be collected periodically and provided to a healthcare professional. By collecting the user data while at the user's home, the scale is used to improve patient engagement with treatment or diagnosis by instructing the user, reminding the user of various actions (reminders to take prescriptions, to have shots, reminders of upcoming appointments, etc.), and providing feedback to the user and the healthcare professional, such as a nurse or a physician.

As a specific example, the scale reminds the user that their surgery is the next day and instructs the user to not eat or drink after 10 pm that evening. In other aspects, the scale helps the user with their treatment by reminding them when to take medications and/or shots, such as for fertility or diabetes treatments. Users can be provided incentives to complete the instructed actions and/or goals, which is provided by advertisers in exchange for providing advertisements using the scale. The scale can output the scale-obtained data to the healthcare professional as feedback. The feedback includes improvements (or lack of improvements) in physiological-related data, indication of compliance with treatment, and/or tracking of physiological data. The scale can provide feedback to the user including tracking improvements (or lack of improvements) in physiological-related data and suggestions or recommendations to improve their health.

The above discussion/summary is not intended to describe each embodiment or every implementation of the present disclosure. The figures and detailed description that follow also exemplify various embodiments.

BRIEF DESCRIPTION OF THE DRAWINGS

Various example embodiments may be more completely understood in consideration of the following detailed description in connection with the accompanying drawings, in which.

Figure 1:
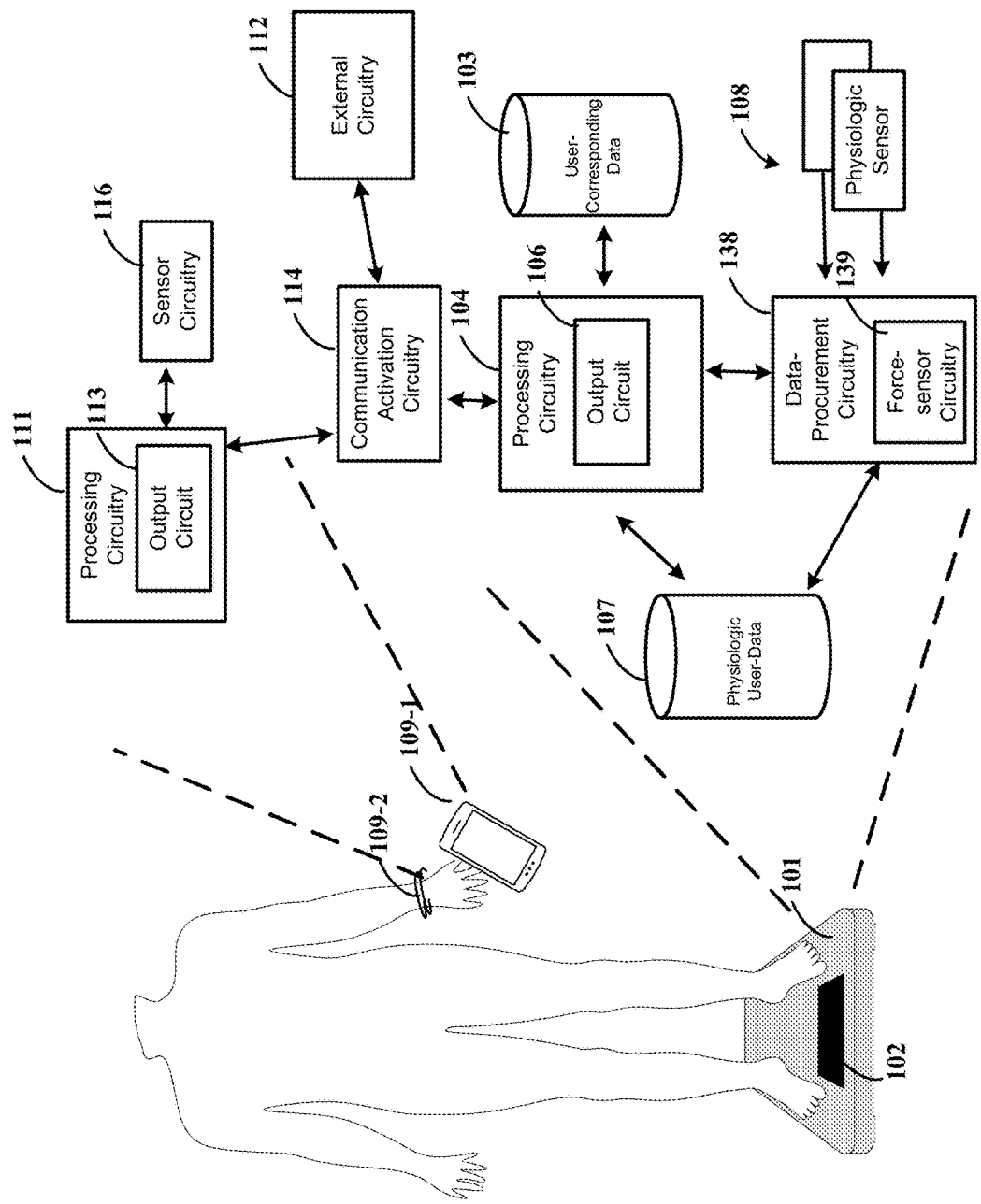
FIG. 1 shows an apparatus consistent with aspects of the present disclosure.

While various embodiments discussed herein are amenable to modifications and alternative forms, aspects thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DESCRIPTION

Aspects of the present disclosure are believed to be applicable to a variety of different types of apparatuses, systems, and methods involving a scale-based on-demand care system. In certain implementations, aspects of the present disclosure have been shown to be beneficial when used in the context of a system, including a weighing scale, one or more other user devices, a standalone user CPU, and the world-wide-web. In specific embodiments, the scale is a portion of an on-demand care system that acts as a hub for collecting user data from various user devices, such as cardio-related data, exercise data, and/or food or liquid tracking data, among other data. In further specific embodiments, the scale-obtained data is combined with other user data from medical devices, such as thermometers, oxygen level devices, blood-sugar monitoring devices, and heart rate monitors, etc. A healthcare professional, such as a nurse, physician and/or other staff, can enter results from various tests to the scale via a user device, such as a cellphone and/or tablet with an application. The data from the various sources is combined and used to medically assess the user. In various embodiments, the scale outputs the data to another source, such as an entity with physicians available for diagnosis purposes, and the other source provides diagnosis of the user based on the aggregated data. The on-demand care system is mobile and can be used in various instances to provide low cost healthcare services and/or services to a remote location.

In various specific embodiments, the scale-based on-demand care system is used by a particular patient to provide additional data to a healthcare professional, such as a nurse and/or a physician, and to increase patient engagement with their treatment. For example, the scale is in communication with other user devices and/or medical devices to collect and aggregate various user data. Additionally, the healthcare professional communicates instructions via a user device to the scale based on treatment of the user and/or parameters to track. The scale is updated with the data and provides various reminders to the user, such as reminders of a prescription to take, upcoming appointments and/or surgeries, and goals. The scale tracks the user's progress and provides potential and/or suggested correlations based on the scale-obtained data, such as changes in lifestyle and improvements in cardio-related data. The scale provides the tracked data and potential/suggested correlations to the circuitry that the healthcare professional can access such that the healthcare professional is aware of improvements and/or issues that may be occurring. A physician and/or other healthcare professional is able to assist the user in advancing and/or improving their health and identifying potential issues (such as drug reactions or titration issues) prior to significant health problems for the user. Further, the user is provided with the tracked data and suggested correlations so that the user can see improvements (or changes) to their health and potential areas for further improvement. These and other aspects can be implemented to address challenges, including those discussed in the background above. While not necessarily so limited, various aspects may be appreciated through a discussion of examples using such exemplary contexts.

In various specific embodiments, the scale-based on-demand care system includes at least one scale, the Internet (e.g., world-wide-web), a standalone user CPU, and one or more user devices, such as a smartwatch, fitness tracking device, smartphone, and/or smartbed, among other devices. The scale collects user data which may be sensitive to the user, such as cardiogram data and data indicative of disorders and disease, and other user data, such as demographic information and weight. The one or more user devices include devices that collect various user data, such as exercise data, food intake or liquid intake data, sleep data, and/or cardiogram data, among other information. The standalone user CPU includes a user device having processing circuitry and/or a user display that is easier for the user to view data than the scale or other user devices. The standalone user CPU and other user devices form a robust graphical user interface (R-GUI) for the user to view various data. In some embodiments, the standalone user CPU includes a personal computer, a laptop, a tablet, and/or a smartphone.

Embodiments of the present disclosure are directed to a platform apparatus that provides various features including communicating with other user devices, such as a smartwatch, smartphone, smartbed and/or smartcup, to aggregate and communicate user data. The platform apparatus, such as a body weight scale, provides various features such as collecting scale-obtained data from a user while the user is standing on the platform apparatus, aggregating user data from a plurality of other user devices with the scale-obtained data, and outputting the aggregated user data to external circuitry using a secure connection to a server. In various embodiments, the aggregated user data is output in response to verifying a scale-based biometric from the user. The platform apparatus includes hardware security circuitry, such as a hardware token that provides a hardware key to provide additional security. The user data is provided to the scale from the user devices in response to secure access to the scale via a scale-based biometric and is output to the external circuitry, such as a standalone CPU and/or a server CPU, in response to the scale-based biometric In various embodiments, the scale includes trigger data. The trigger data includes user data values and/or combinations of different data values with user demographic information that indicates that the user is at risk for a condition, such as a disorder or disease. In response to the trigger data and the scale-obtained data or other user data from the other devices indicating that the user is at risk for a condition, the scale and/or standalone user CPU filters the user data from the scale and the other user devices and filters data from the Internet to identify data that is relevant to the condition. In this manner, the system is used as a medical analytic driver that filters scale-obtained data, user device-obtained data, and data from the Internet to identify data related to the condition. The system can provide the data to a healthcare professional to identify potential issues and correlations prior to symptoms fully developing and/or a hospital visit.

For example, the aggregated data from the scale and the one or more user devices and/or medical devices can be compared to trigger data to determine if the user is at risk for a condition. The trigger data is stored directly on a memory circuit of the scale and/or is stored on a memory circuit of the standalone user CPU (and accessible by the scale). The trigger data includes values of various user data that indicate that the user is at risk for a condition (e.g., has a likelihood above a particular threshold of having or being at risk for the condition). In response to a match with the trigger data, the scale or standalone user CPU optionally indicates a potential risk to the user and filters the user data for data correlated with the condition and filters the Internet for various data regarding the condition and/or matching the filtered user data. For example, the risk can be identified by comparing user data to population normal range for the user demographic and/or the user's historical range (e.g., a normal range) or a range established by a healthcare professional. The resulting data is output to circuitry that a healthcare professional can access to assist the healthcare professional in medically assessing the user (on the spot) and/or identifying potential issues for a patient in treatment. For example, in various embodiments, the healthcare professional is at the same location as the user or at a different location.

In response to the filters, the system can provide the user with various additional health information regarding the user, such as information indicative of a condition of the user. The healthcare professional (and/or the user) is provided access to the data using the Internet and/or external circuitry, such as server CPU or standalone CPU that is accessible by the healthcare professional. In response to the healthcare professional providing instructions (such as a confirmed diagnosis and/or the additional health information), the scale is modified with the instructions. The modification, in some embodiments, includes storing, on the scale, various prompts or data to provide the user, such as reminders of prescriptions, tests, and/or dietary restrictions, correlation data (e.g., diagnosis data), adding additional devices and/or parameters to track, and/or health information about the condition of the user (e.g., articles), among other data. Furthermore, the standalone user CPU of the on-demand care system, in some embodiments, is used to display various data to the user, such as generic health information, user-specific diagnosis data, blogs/forums of social groups, physician reports, and/or studies, among other information.

As a specific example, in response to the filter, the scale-obtained data and/or the scale itself is used to further assess the condition of the user and/or to obtain additional information. For example, the user views various data, such as generic health information about the condition, articles about the condition, blogs, and/or forums of social groupings that are identified using the filter. The scale is used to further assess the condition of the user by performing additional tests and/or asking the user questions via a user interface of the scale and/or other user device. In various embodiments, the user data is provided to a physician to confirm the diagnosis. In response to confirmation of the diagnosis, the scale is modified with the confirmed diagnosis. Optionally, the scale is modified to aggregate data from additional devices, such as an ECG tracking device, and/or to obtain additional parameters, such as prescription drug titration, weight loss monitoring and/or goals, exercise goals, and/or a stress test.

The user data obtained by the scale can be based on sensing, detection, and quantification of at least two simultaneously acquired impedance-based signals. The simultaneously acquired impedance-based signals are associated with quasi-periodic electro-mechanical cardiovascular functions, and simultaneous cardiovascular signals measured by the impedance sensors, due to the beating of an individual's heart. The measured signals are used to determine at least one cardiovascular related characteristic of the user for determining the heart activity, health, or abnormality associated with the user's cardiovascular system. The sensors can be embedded in a user platform, such as a weighing scale-based platform, where the user stands stationary on the platform and with the user's feet in contact with the platform, such that the impedance measurements are obtained when the user is standing on the platform with bare feet.

In certain embodiments, the plurality of impedance-measurement signals includes at least two impedance-measurement signals between one foot and another location. Further, in certain embodiments, a signal is obtained based on a timing reference, which is indicative of synchronous information and that corresponds to information in a BCG. Additionally, the methods can include conveying modulated current between selected ones of the electrodes. The plurality of impedance-measurement signals may, for example, be carried out in response to current conveyed between selected ones of the electrodes. Additionally, the methods, consistent with various aspects of the present disclosure, include a step of providing an IPG measurement within the one foot. Additionally, in certain embodiments, the two electrodes contacting one foot of the user are configured in an inter-digitated pattern of positions over a base unit that contains circuitry communicatively coupled to the inter-digitated pattern. The circuitry uses the inter-digitated pattern of positions for the step of determining a plurality of pulse characteristic signals based on the plurality of impedance-measurement signals, and for providing an IPG measurement within the one foot. As discussed further herein, and further described in U.S. patent application Ser. No. 14/338,266 filed on Oct. 7, 2015, which is herein fully incorporated by reference for its specific teaching of inter-digitated pattern and general teaching of sensor circuitry, the circuitry can obtain the physiological data in a number of manners.

In medical (and security) applications, for example, the impedance measurements obtained from the plurality of integrated electrodes can be used to provide various cardio-related information that is user-specific including (as non-limiting examples) synchronous information obtained from the user and that corresponds to information in a ballisto-cardiogram (BCG) and impedance plethysmography (IPG) measurements. By ensuring that the user, for whom such data was obtained, matches other bio-metric data as obtained concurrently for the same user, medical (and security) personnel can then assess, diagnose and/or identify individuals with high degrees of confidence and accuracy.

In a number of specific embodiments, the user stands on the scale. The scale, in response, transitions from a low-power mode of operation to a higher-power mode of operation. The scale may attempt to establish communication with another user device. However, the communication is not activated until authorization data is obtained by the scale from the user device and/or until a scale-based biometric is identified. From the collected signals, the scale identifies a scale-based biometric corresponding with the user and validates the various user data generated as corresponding to the specific user and associated with a user profile. Other devices, such as other user devices, medical devices, and/or testing devices are used to collect signals and/or other user data from the user. The data collected from the scale and the other devices, in various embodiments, is used to provide on-demand care to the user.

The scale and other devices can be operated as part of an on-demand health-care clinic, such as a traveling clinic, low-cost clinic, clinic at a retail location, and/or a remote clinic. The aggregated data is provided to a healthcare professional for diagnosis purposes. In some embodiments, the healthcare professional is at a remote location and the aggregated data is output, such as using the scale or a standalone CPU in communication with the scale, to the remote location. In other embodiments, the healthcare professional is at the location of the scale to provide on the spot diagnosis and/or recommendations. The scale or standalone CPU, using trigger data (e.g., thresholds), can analyze the aggregate data and filter the Internet and/or a research database to provide suggested diagnoses and/or recommendations to the healthcare professional. Thereby, the on-demand care system is used as a medical analytic driver to assist the healthcare professional in diagnosing and/or otherwise advising the user and to reduce cost of healthcare services. For example, in specific embodiments, the healthcare professional is a nurse and the scale provides feedback to the nurse on whether to recommend the user to see a physician or not.

In other related and specific embodiments, the scale is located at the dwelling of the user and used to improve patient engagement with a treatment plan and/or to improve their health condition. For example, the healthcare professional communicates with the scale, via circuitry, to provide various instructions and the scale is updated with the instructions. The instructions include diagnosis data, treatment plans, identification of prescription to take, upcoming appointments, dietary restrictions and/or recommendations, exercise restrictions and/or recommendations, physiological goals, etc. The scale, using the instructions, reminds the user of information about their treatment plan by providing a reminder and/or other instruction when the user approaches or stands on the scale and based on the instructions from the healthcare professional. The scale (or external CPU in communication) can track various parameters, including scale-obtained data and physiological data determined using the scale-obtained data, and parameters obtained from other user devices and/or medical devices over time and identify potential correlations between physiological data (e.g., improvements or changes) and other user data (e.g., lifestyle data, such as diet, exercise, sleep habit, or changes in one type of physiological data effecting another).

The tracked data is provided to the healthcare professional such that the healthcare professional is aware of the user's progress and how the user is conforming to the treatment plan. Further, the potential correlations are provided to the healthcare professional to assist the professional in analyzing how the user is doing and potentially diagnosing or adjusting the treatment plan. The user is also provided with the tracked data and/or potential correlations so that the user is educated on their health condition and progress they have made. By providing the healthcare professional with tracked data, obtained while the user is located in their dwelling, potential health issues may be identified prior to an emergency and/or prior to symptoms being experienced by the user. For example, the healthcare professional may identify an issue with the prescription drug dosage and/or interactions between prescriptions before the user has symptoms causing a hospital visit and/or for preventing or mitigating misdiagnosis. Further, feedback can be provided to the user to inform the user on how to modulate a known (e.g., diagnosed) condition and/or how to generally improve their health (without identifying the actual risk) via lifestyle changes.

Turning now to the figures, FIG. 1 shows an apparatus consistent with aspects of the present disclosure. The apparatus includes a scale and one or more user devices (e.g., device 109-1 and/or 109-2) and, optionally, one or more medical devices. The scale and user devices/medical devices can communicate various cardio-related data and/or other user data. The scale collects and aggregates user data from the scale, the user devices, and/or medical device(s). The scale is used to securely communicate with external circuitry 112, such as a standalone CPU and/or server CPU. For example, the scale verifies identification and authorization of the communication using a scale-obtained biometric. In other embodiments, the scale is a portion of a clinic, such as a traveling clinic or low-cost clinic, the data obtained by the scale and the user devices/medical devices is aggregated and used to diagnosis and/or medically assess the user.

In various specific embodiments, the external circuitry 112 is accessible by a healthcare professional associated with the user and instructions related to a treatment plan or condition of the user are sent from the external circuitry 112 to the scale. The scale is modified/updated with the instructions. The instructions include various information about the condition of the user and a treatment plan of the user. For example, the scale can be located within the dwelling of the user and used to provide various instructions to the user related to a treatment plan. The scale or other external circuitry can provide reminders to the user, where the reminders are specific to a treatment plan and based on instructions provided by a healthcare professional. The scale tracks scale-obtained data, and other user data from the other user devices and optionally the medical devices, and correlates changes in the user (physiological) data with various factors, including lifestyle changes, prescription medication, surgery, etc. Further, the scale outputs various data to circuitry accessible by the healthcare professional for review.

The scale communicates the aggregated user data to the external circuitry 112 so that the healthcare professional is able to provide healthcare services, track the progress of the user and/or track how well the user has followed the treatment plan. Updating the scale based on a treatment plan or condition of the user, in a number of embodiments, allows for additional user engagement with the treatment plan. Further, by tracking and outputting data back to the external circuitry 112, the healthcare professional and user are provided with feedback on how the treatment plan is working (or not working), potential issues, and/or potential correlations to improvements or issues. The feedback can inform the user on how to modulate a known (e.g., diagnosed) condition and/or how to generally improve their health (without identifying the actual risk) via lifestyle changes.

Alternatively and/or in addition, the scale-based on-demand care system is used by a healthcare professional to medically assess patients. For example, a healthcare professional uses the scale-based on-demand care system to provide healthcare services to patients, such as at a low-cost clinic, retail clinic or other walk-in type clinic, a temporary clinic or a movable clinic that can be used in remote locations. The scale aggregates scale-obtained data with other user data from medical devices and provides various correlations to the healthcare professional. In some embodiments, the aggregated data is compared to trigger data to identify potential diagnosis and/or conditions of the user and to filter the Internet and/or a research database to identify meaning. In various specific embodiments, the scale (or standalone CPU in communication with the scale) can flag data that is out of bounds based on the trigger data. For example, the trigger data can include thresholds, such as a population normal range for a physiological parameters that is specific to the user's demographic and/or the user's historical range (e.g., a normal range) or a range established by a healthcare professional. The results are provided to the healthcare professional to assist in medically assessing the user and/or identifying if additional assistance, such as an in-person visit to a physician and/or hospital, is needed.

User data, as used herein, includes or refers to data obtained by the scale and/or the user device that is related to user health, lifestyle, and/or identification of the user. In various embodiments, the scale, the user devices, and/or the medical devices collect various user data. For example, both the scale and the user device collect cardio-related data. Alternatively, the user device collects exercise data and/or sleep data, among other data. The medical devices can collect various physiological data and/or test results from the user. Combining the user data from the scale, the user devices, and the medical device is beneficial in identifying various risks of the user for conditions, in tracking the user's progress, and/or in making suggestions to the user.

The scale can include a platform 101 and a user display 102. The user, as illustrated by FIG. 1 is standing on the platform 101 of the apparatus. The user display 102 is arranged with the platform 101. As illustrated by the dotted lines of FIG. 1, the apparatus further includes processing circuitry 104, data-procurement circuitry 138, physiologic sensors 108, communication activation circuitry 114, and an output circuit 106. That is, the dotted lines illustrate a closer view of components of the apparatus.

The physiologic sensors 108 can include a plurality of electrodes integrated with the platform 101. The electrodes and corresponding force-sensor circuitry 139 are configured to engage the user with electrical signals and to collect signals indicative of the user's identity and cardio-physiological measurements while the user is standing on the platform 101. For example, the signals are indicative of physiological parameters of the user and/or are indicative of or include physiologic data, such as data indicative of a BCG or ECG and/or actual body weight or heart rate data, among other data. As discussed further below, the signals can be force signals. The user display 102 is arranged with the platform 101 and the electrodes to output user-specific information for the user while the user is standing on the platform 101. The processing circuitry 104 includes CPU and a memory circuit with user-corresponding data 103 stored in the memory circuit. The processing circuitry 104 is arranged under the platform 101 upon which the user stands, and is electrically integrated with the force-sensor circuitry 139 and the plurality of electrodes (e.g., the physiologic sensors 108).

The data indicative of the identity of the user includes, in various embodiments, user-corresponding data, biometric data obtained using the electrodes and/or force sensor circuitry, voice recognition data, images of the user, input from a user's device, and/or a combination thereof and as discussed in further detail herein. The user-corresponding data includes information about the user (that is or is not obtained using the physiologic sensors 108,) such as demographic information or historical information. Example user-corresponding data includes height, gender, age, ethnicity, exercise habits, eating habits, cholesterol levels, previous health conditions or treatments, family medical history, and/or a historical record of variations in one or more of the listed data. The user-corresponding data is obtained directly from the user (e.g., the user inputs to the scale) and/or from another circuit (e.g., a smart device, such as a cellular telephone, smart watch and/or fitness device, cloud system, etc.). The user-corresponding data 103 is input and/or received prior to and/or in response to the user standing on the scale.

In various embodiments, the processing circuitry 104 is electrically integrated with the force-sensor circuitry 139 and the plurality of electrodes and configured to process data obtained by the data-procurement circuitry 138 while the user is standing on the platform 101. The processing circuitry 104 can generate cardio-related physiologic data 107 corresponding to the collected signals and that is manifested as user data. Further, the processing circuitry 104 generates data indicative of the identity of the user, such as a scale-based biometric, a user ID and/or other user identification metadata. The user ID is identified, for example, in response to confirming the identification of the user using the collected signals indicative of the user's identity (e.g., a scale-based biometric).

In specific embodiments, in response to the user standing on the platform 101, the processing circuitry 104 transitions the scale from a reduced power-consumption mode of operation to at least one higher power-consumption mode of operation. The processing circuitry 104 identifies a scale-based biometric of the user using the collected signals. For example, the scale-based biometric includes foot length, foot width, weight, voice recognition, facial recognition, and a combination thereof. In various embodiments, the scale-based biometric corresponds to a user ID and is used to verify the identity of the user. Using the scale-based biometric, the user data is validated as concerning the user associated with the scale-based biometric. The user data includes data indicative of the user's identity and the generated cardio-related physiologic data.

The one or more user devices, e.g., device 109-1, 109-2, and/or the medical device, are not integrated within the scale and can include a cellphone, a smartwatch, other smart devices, a tablet, a (photo) plethysmogram, a two terminal ECG sensor, and a combination thereof. Each user device and medical device includes processing circuitry 111 and an output circuit 113. Optionally, one or more user devices and/or medical devices includes sensor circuitry 116. The user devices and/or medical devices collect various signals. For example, the user device and/or medical device collects signals indicative of the user's identity. The collected signals indicative of the user's identity include the authorization data to authorize use of the user device and/or medical device and, optionally, is sent to the scale to authorize communication. For example, the user device and/or medical device identifies the authorization data of the user using the collected signals indicative of the user's identity and, therefrom, validates the collected signals as concerning the user associated with the authorization data and/or a user profile.

Example authorization data includes data selected from the group consisting of a password, a passcode, a biometric, a cellphone ID, and a combination thereof. Example biometrics in various embodiments, includes biometrics selected from the group consisting of: a finger print, voice recognition, facial recognition, DNA, iris recognition, typing rhythm, and a combination thereof, in various embodiments.

A medical device, as used herein, includes or refers to specialized circuitry designed to monitor and/or track particular data. For example, the one or more medical devices monitor physiological data and/or are used to obtain test results. Further, in specific aspects, one or more of the medical devices collect the respective physiological data and communicate the physiological data to the scale. Example medical devices include a heart monitor, a blood pressure monitor, a blood sugar monitor, an oxygen photoplethysmogram, among other devices. The results from one or more of the medical devices can be communicated with the scale via a healthcare professional entering the data into a standalone CPU, such as a smartphone, tablet, and/or laptop, and the standalone CPU communicates the data to the scale.

The scale can optionally receive the authorization data and, in response to both the authorization data and the scale-based biometric corresponding to the user, activates communication between the scale and the user devices/medical devices. For example, the scale includes a communication activation circuitry 114 to activate the communication. The communication activation circuitry 114, in some embodiments, includes an AND gate to activate the communication in response to receiving both the identified scale-based biometric and the authorization data that correspond to the same user. Although embodiments are not so limited and the communication activation circuitry can include various circuit components and/or processing circuitry to activate the communication and/or verify both the scale-based biometric and the authorization data correspond to the specific user. Further, the communication is activated in response to identification of the scale-based biometric and verification of the user device based on data in a user profile corresponding with the user (e.g., identification of the user device) and/or within the user data sent by the user device/medical device.

In response to the activation, the user device and/or medical device outputs user data to the scale. The output circuit 106 can receive the user data from the user device/medical device and, in response, can output the user data to the processing circuitry 104. In various embodiments, the output circuit 106 displays on the user display 102 the user's weight and the data indicative of the user's identity and/or the generated cardio-related physiologic data corresponding to the collected signals. The communication, in various embodiments, includes a wireless communication and/or utilizes a cloud system.

The scale receives the user data and validates the user data as concerning a specific user. Each user can be associated with a user profile (based on the communication activation and/or a user ID within the user data), such as using authorization data and/or other identifying data in the user data. For example, a user can input user data to one or more of the user devices.

The scale can aggregate the user data obtained by the scale with the user data from the one or more user devices and the medical devices. For example, the aggregation includes combining and/or correlating the data. In addition, the scale securely communicates the aggregated user data to external circuitry 112 using a secure connection to a server, by verifying the communication using a scale-obtained biometric, and/or by performing additional security measures on the data.

In various embodiments, the scale correlates portions of the user data obtained by the scale with the user data obtained by the user devices and/or medical devices. The correlation includes placing the data in phase, in the same and/or similar time range, in the same and/or similar time scale, and/or other correlation. Although embodiments are not so limited, and a standalone CPU can perform the additional processing. For example, in some specific embodiments, the user data obtained by the scale can include or be indicative of a BCG of the user and user data obtained by the user device (or plug-in device) can include or be indicative of an ECG of the user. The correlation can include correcting the data to get true phase change between the BCG and ECG. In other embodiments, the scale can collect an ECG from a different location than an ECG collected by the user device. The correlation includes placing the ECG data from the scale in phase with the ECG data from the user device, such that the two cardiogram waveforms correspond to one another. In other embodiments, the data includes time stamps and the correlation includes mapping the two data sets based on the time stamps. In various embodiments, the correlated user data and collected signals are stored within a user profile corresponding to the user, such as a user profile stored on the scale.

The scale can be located in the user's dwelling and used to assist the user in treatment. For example, a healthcare professional, via external circuitry 112, communicates with the scale and provides various treatment instructions. The treatment instructions include general information and/or specific instructions related to the user and treatment of the user. The treatment instructions include general lifestyle recommendations (e.g., weight loss, increase exercise), specific dietary and/or exercise requirements, sleep habit recommendations, upcoming treatments, prescription medication schedule, etc. The scale is modified with the treatment instructions by storing the instructions on the scale. The scale then prompts the user with the various instructions, such as by providing a display and/or computer-generated voice messages. For example, the scale provides a projection of data when the user approaches or steps on the scale reminding the user "Your Medication A should be taken in the morning, have you taken your medication?"

In various embodiments, the scale provides the data via a foot-controlled user interface (FUI). An FUI, as used herein, includes a user interface that allows the user to interact with the scale via inputs with the user's foot. The user can interact with the scale by moving their foot relative to the platform of the scale. The FUI can be used to provide the user with data via a display on the user interface of the scale, a projection of user data and/or computer-generated voice messages. A projection of data, includes a display via a projection circuitry of the scale that projects the display to a surface that is external to the scale. In specific embodiments, the projection circuitry includes one or more light-emitting diodes (LEDs). For example, the projection circuitry is a digital light processing (DLP) projector that includes an LED and a Digital Micromirror Device (DMD), a Liquid Crystal Display (LDC) projection that includes a prism or series of dichroic filters, and/or a Liquid Crystal on Silicon (LCOS) that includes a liquid crystal layer on top of silicon backplane, such as a pico projector, among other projection circuitry.

By collecting the user data while at the user's home, the scale is used to improve patient engagement with treatment or diagnosis by instructing the user, reminding the user of various actions, and providing feedback to the user and the healthcare professional. In some specific embodiments, the scale-obtained data is reviewed, such as by a nurse or a physician, to determine if the user should visit a physician.

The system can thereby be used to prevent or mitigate visits to a physician that are not needed, and potentially reduce healthcare costs for the patient and/or an insurance company. As a more specific example of feedback, the scale reminds the user that their surgery is the next day and instructs the user to not eat or drink after 10 pm that evening. In other embodiments, the scale helps the user with their treatment by reminding them when to take medications and/or shots, such as for fertility treatments. Users, in various aspects, are provided incentives to complete the instructed actions and/or goals, which is provided by advertisers in exchange for providing advertisements using the scale.

The scale-based system (e.g., the scale, standalone CPU, or server CPU) can track the scale-obtained data and user data from the other user devices/medical devices over time. The scale-based system can identify potential correlations between changes in physiological data and other data associated with the user, such as lifestyle changes, prescription medication, etc. The potential correlations and tracked scale data is provided to the user and/or the healthcare professional. The user is able to have additional engagement with their treatment plan and see the progressed results caused by the treatment plan. Further, the healthcare professional is able to see how the user is progressing, if the user is following the treatment plan, and identification of potential problems prior to symptoms appearing (or severe symptoms appearing). As a particular example, a user on dialysis with heart related problems, may have multiple prescriptions they are taking that are difficult for healthcare professionals to titrate and the prescription can have interactions with one another. The multiple prescriptions may cause the user unintended consequences and symptoms, that without additional information, may appear to be a disorder (such as, Alzheimer's). The tracked scaled data and potential correlations are provided to the healthcare provider to identify potential issues and to potentially prevent an incorrect diagnosis.

In a number of embodiments, the scale is configured to collect data from a plurality of users. In such embodiments, the scale differentiates between the different users based on scale-based biometrics and/or input data to the scale from another device. Differentiating between the two or more users and automatically communicating (e.g., without further user input) user data responsive to scale-obtained biometrics, in various embodiments, provides a user-friendly and simple way to communicate data from a scale while avoiding and/or mitigating unintentional (and/or without user consent) communication. For example, the scale, such as during an initialization mode for each of the two or more users, collects user data to identify the scale-based biometrics and stores an indication of the scale-based biometrics in a user profile corresponding with the respective user. During subsequent measurements, the scale recognizes the user by comparing collected signals to the scale-based biometrics in the user profile. The scale can compare the collected signals to each user profile of the two or more users and identifies a match between the collected signals and the indication of the scale-based biometrics. A match can be within a range of values of the indication stored. Further, in response to verifying the scale-based biometric(s), a particular communication mode is authorized. In accordance with various embodiments, the scale uses a cardiogram of the user and/or other scale-based biometrics to differentiate between two or more users.

The scale can communicate the aggregated user data by authorizing the communication based on the biometric identified and adding various security measures to the user data in response to the authorized communication. For example, in various embodiments, the user profiles are associated with a hierarchy of different levels of biometrics that enable different data to be communicated and/or enable communication of data to different sources. For example, in response to verifying a first biometric, the scale outputs the user's weight to the user's smartphone or other standalone CPU. In response to verifying a second biometric, the scale outputs additional data to external circuitry that is more sensitive, as discussed further herein. For example, a highest-sensitivity biometric of the scale is used to authorize communication of tracked user data and potential correlations to circuitry that a healthcare professional can access.

Using the scale as a hub to collect various user data and to communicate the user data to external circuitry for medical assessment, automatically and without user input, can reduce the time for a user to output various user data for correlation and processing. Further, as the scale is not accessible by other circuitry and/or may not include additional applications, the scale is less likely to be accessed by others, as compared to the user devices. For example, the scale accesses user data only in response to verifying the user using a scale-based biometric, in some embodiments.

For example, in specific embodiments, in response to the user standing on the scale, the scale transitions from the reduced-power mode of operation to the higher-power mode of operation and collects signals indicative of the user's identity. In response to the transition, the scale collects signals indicative of cardio-physiological measurements (e.g., force signals). The processing circuitry 104 identifies a scale-based biometric using the collected signals and processes the signals to generate cardio-related physiologic data manifested as user data. Further, the processing circuitry validates user data, which includes data indicative of the user's identity and the cardio-related physiologic data, as concerning the user associated with the scale-based biometric. Optionally, the validation includes correlating the user data with a user ID in response to the validation. During, after, and/or before the identification of the scale-based biometric, the user device/medical device collects signals indicative of the user's identity and, therefrom, identifies authorization data corresponding to the user and user data. The user device communicates the user data, and, optionally the authorization data to the scale. In response to verifying the user data from the user device and/or medical device is correlated with the user, the scale aggregates the user data from the user device with the scale obtained data, identifies potential risks or correlations using trigger data, and filters the Internet to identify a potential diagnosis. The resulting data is provided to a healthcare professional for on-demand care.

Alternatively and/or in addition, the scale tracks user data from the scale, the user devices, and/or medical devices over time and identifies potential correlations to changes in the user's physiological state (e.g., parameter changes). The potential correlations and tracked changes are provided to the healthcare professional and/or the user to identify progress and/or regression of the user's health and potential causes and/or solutions. The healthcare professional modifies the scale by outputting various instructions related to a treatment plan of the user. The scale, using the output instructions, is used to remind the user regarding the treatment plan and encourage the user to reach goals and/or habit changes. The scale outputs feedback data to the healthcare professional that indicates the user's progress and indicates whether the user is following the treatment plan. The healthcare professional is able to view physiological data indicative of the user's reaction to the treatment plan prior to the user visiting the professional or having issues and can revise the treatment plan based on the feedback.

Figure 2:
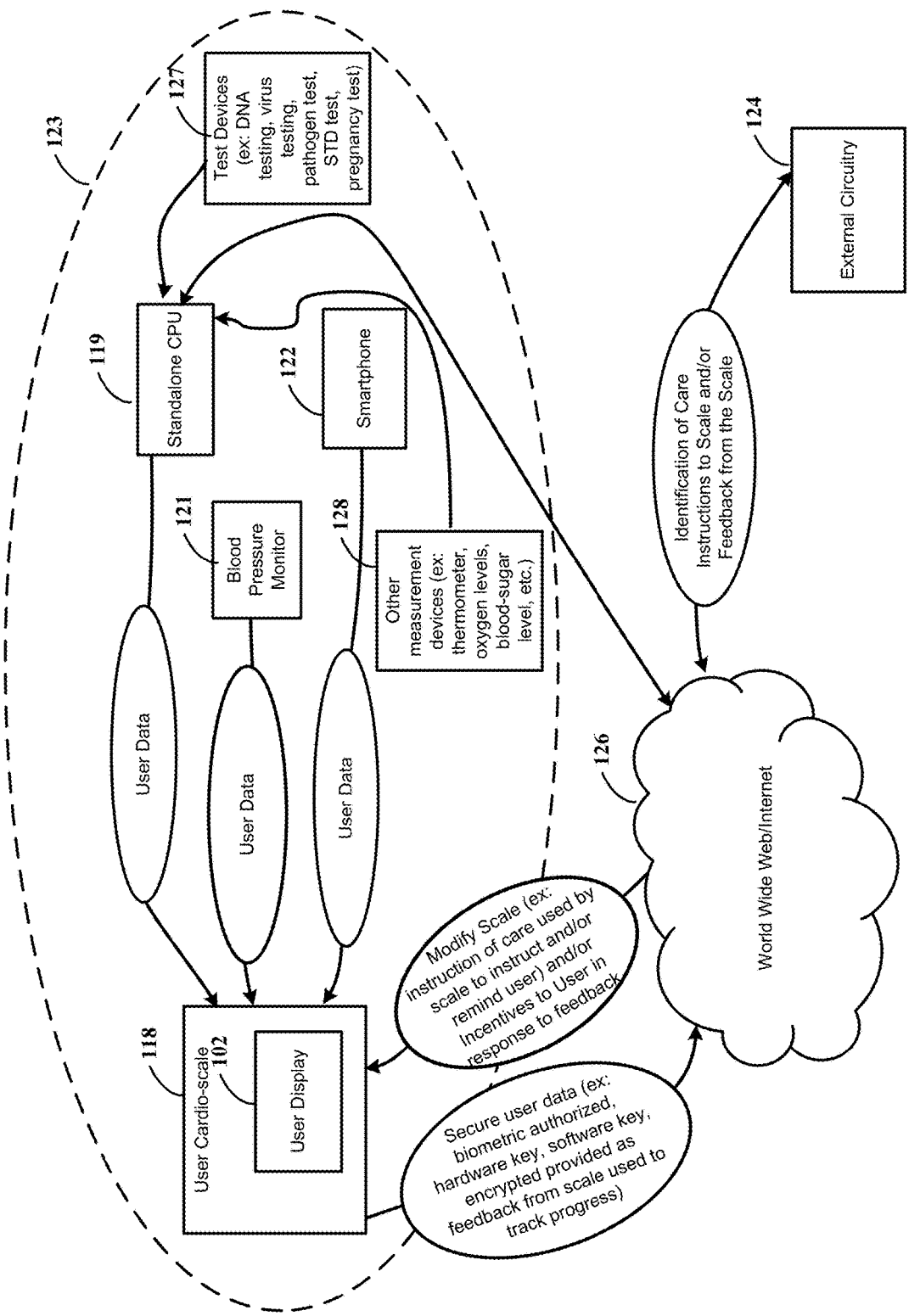
FIG. 2 shows an example of a scale-based on-demand system consistent with aspects of the present disclosure.

FIG. 2 shows an example of a scale-based on-demand care system consistent with aspects of the present disclosure. As illustrated, the scale-based on-demand system includes at least one scale 118, the Internet (e.g., world-wide-web) 126, a standalone user CPU 119, and one or more user devices, such as a smart watch, fitness tracking device, smartphone 122, smartbed, among other devices, such as medical devices 128 and test devices and/or results 127.

As previously discussed, the scale 118 collects user data, such as cardiogram data and data indicative of disorders and disease, and other user data, such as demographic information and weight. The scale 118 displays data, such as user weight, prompts or notifications, and other information using a user interface, such as an FUI. The one or more user devices include devices that collect various user information, such as exercise data, food intake or liquid intake data, sleep data, cardiogram data, among other information. The standalone user CPU 119 includes a user device that includes additional processing resources and/or a user display that is easier for the user to view data than the scale or other user devices. Thereby, the standalone user CPU 119, and other user devices form a robust graphical user interface (R-GUI) for the user to view various data. In some embodiments, the standalone user CPU 119 includes a personal computer, a laptop, a tablet, and/or a smartphone.

Optionally, the system includes one or more medical devices 128 and one or more test devices 127. The medical devices include circuitry and are configured to collect particular physiological data from the user. Example medical devices include a thermometer, oxygen level devices, blood-sugar monitoring devices, and/or blood pressure devices, among other devices. The test devices 127 include circuitry configured to output a result of a physiological test. Example test device outputs include a DNA test, virus test (e.g., flu test and/or other viruses), pathogen test (e.g., E. coli), sexually transmitted disease test, and pregnancy test. In some embodiments, one or more of the medical devices and/or the test devices communicate the collected physiological data or test results directly to the scale 118 using a wired or wireless communication. Alternatively, the user and/or a healthcare professional enters the physiological data and/or test results to the scale, such as using the standalone CPU 119, a smartphone 122, and/or a tablet.

In various embodiments, the scale 118 includes trigger data. The trigger data includes user data values and/or combinations of different data values with user demographic information that indicates that the user has a risk for a condition (e.g., threshold values as previously described), such as a disorder or disease. In response to the trigger data and the scale-obtained data or other user data from the other user devices and/or medical devices indicating that the user has a risk for a condition, the scale, standalone CPUP 119 or server CPU (responsive to a communication from the scale) filters the Internet 126 and/or a research database.

For example, the aggregated data from the scale 118 and the one or more user devices, medical devices, and test devices is compared to trigger data to determine if the user is at risk for a condition. The trigger data is stored directly on a memory circuit of the scale 118 and/or is stored on a memory circuit of the standalone user CPU 119 (and accessible by the scale or the CPU 119 performs the processing). The trigger data includes values of various user data that indicate the user has a likelihood above a particular threshold of having and/or being at risk for a condition. In response to a match with the trigger data, the scale and/or CPU filters the user data for data correlated with the condition and filters the Internet 126 for various data regarding the condition and/or matching the filtered user data. In this manner, the on-demand care system is used as a medical analytic driver that filters scale-obtained data, user device-obtained data, medical device-obtained data, test data, and data from the Internet to identify data related to the condition.

In response to the filter(s), a healthcare professional is provided access to the data for diagnosis purposes, in some embodiments. For example, the data is output to external circuitry 124 for access and analysis by a physician and the physician provides diagnosis data back to the scale. Alternatively and/or in addition, the healthcare professional is present with the user and accesses the data through the standalone CPU 119. For example, the system is part of a low-cost healthcare clinic and/or a traveling healthcare clinic. The healthcare professional uses the system to reduce the cost of providing healthcare and increase the number of patients that can be seen.

In some embodiments, the scale is located in the dwelling of the user and used to track user data from the scale, the user devices, and optionally the medical devices and/or tests over time. A healthcare professional modifies the scale based on a treatment plan. The healthcare professional, using external circuitry 124, can provide treatment instructions to the scale. Using the instructions, the scale reminds the user of upcoming appointments, preparation steps for appointments, medications to take, goals to reach, eating habits, and/or sleeping habits, among other reminders.

In various embodiments, the scale provides the above services are part of a subscription model. The services can be provided on a per-use scale or as a subscription. For example, the scale and/or system can be used to provide a hierarchy of services that include different services enabled in response to user selection and activation of subscription levels of different weighted values. The different services can include review of electronically-collected scale data by a physician, diagnosis, tracking and feedback by a physician, on-demand care, in-home patient care (e.g., modifying with treatment plan), among various other services or data provided as a service as described herein.

The scale can track data obtained by the scale, the user device, and optionally the medical devices/test devices over time and identify potential correlations between changes in physiological state of the user and the treatment plan (or lack of following the treatment plan). Example correlations include improvements in physiological parameters due to changes in lifestyle (such as eating habits, exercise habits, sleep habits), medication taken, treatments given, physical therapy, removal or reduction of stress, or changes of other physiological parameters, among other correlations. The scale provides the tracked data and potential correlations to the healthcare professional, via the Internet 126 and the external circuitry 124, for review. For example, the healthcare professional may adjust the treatment plan based on the tracked data/correlations and/or may identify potential issues with the treatment plan. The adjustment can include additional instructions sent to the scale via the circuitry 124. Alternatively and/or in addition, the healthcare professional may contact the user to schedule an appointment. Accordingly, the scale-based on-demand care system provides feedback to the healthcare professional and/or the user regarding the treatment plan for the user and the healthcare professional can adjust the treatment plan with or without seeing the patient.

In some embodiments, the user and/or the scale are used to further assess the condition of the user and/or obtain additional information. The assessment includes the user assessing additional information relating to the condition, using the scale user interface 102 or the R-GUI 123. For example, in response to the filter, the on-demand care system identifies various addition information. The additional information includes various generic health information, articles, blogs/forums or social groupings, and other data identified based on the filter of the Internet using the data that correlates with the condition and the trigger data. The user views the additional information using the interface of the scale and/or R-GUI 123. The scale is used to further assess the condition of the user by performing additional tests (e.g., body-mass-index, QRS complex over time) and/or asking the user questions.

The modification of the scale can include storing, on the scale 118, various correlation data (e.g., diagnosis data), adding additional devices and/or parameters to track (e.g., halter monitor, ECG tracking device, prescription drug titration, weight tracking and/or threshold values, exercise goals, stress test), and/or health information about the condition (e.g., articles), among other data. Furthermore, the standalone user CPU 119 of the system, in some embodiments, is used to display various data to the user, such as generic health information, user-specific diagnosis data, blogs/forums of social groups, physician reports, and/or studies, among other information.

Figure 3:
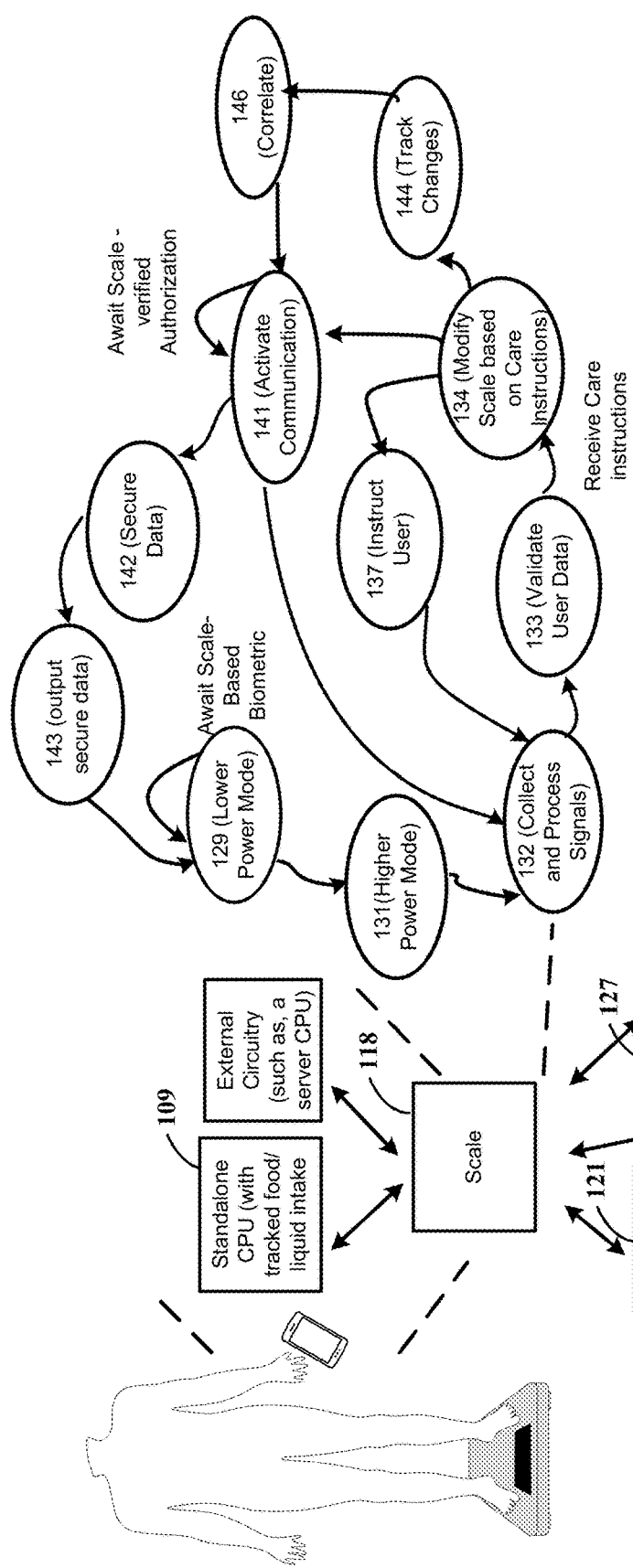
FIG. 3 shows an example of a scale tracking physiological changes of a user based on a treatment plan, consistent with aspects of the present disclosure.

FIG. 3 shows an example of a scale tracking physiological changes of a user based on a treatment plan, consistent with aspects of the present disclosure. As illustrated, a scale 118 is in communication with various user devices 121, 122, 127, and a standalone CPU 109. Optionally, the scale is also in communication with one or more medical devices. The user devices and medical devices, as previously discussed, collect various signals from the user. The scale, illustrated by FIG. 3 can include the scale and the various circuitry illustrated and previously described in connection with FIG. 1. The scale collects various user data obtained by the scale and the user devices and/or medical devices. The user devices 121, 122, 127 further automatically collect various user data, such as sleep data, cardiogram data, exercise data, heart rate data, and food/liquid intake data. In some embodiments, various user data is manually entered by the user to the standalone CPU 109, the scale 118, and/or a smartphone 122. Such data includes user demographic data, food/liquid intake data, and/or sleep data, in some embodiments. In other embodiments, the data includes data from one or more medical devices, which may not be configured to automatically communicate with the scale.

The various user devices 121, 122, 127, and the standalone CPU 109 communicate various user data to the scale 118. The scale 118 aggregates the user data and secures the aggregated user data prior to sending to external circuitry, such as the standalone CPU 109 and/or server CPU. For example, in response to the user standing on the scale, the scale transitions from a reduced power-consumption mode of operation 129 to at least one higher power-consumption mode of operation 131. At 132, the scale collects signals indicative of an identity of the user and cardio-physiological measurements (e.g., force signals) by engaging the user with electrical signals and, therefrom, collecting the signals. Further, at 132, the processing circuitry of the scale, processes the signals obtained by the data-procurement circuitry while the user is standing on the platform and generates, therefrom, cardio-related physiologic data corresponding to the collected signals.

At 133, the processing circuitry of the scale identifies a scale-based biometric of the user using the collected signals and validates the user data, which includes the data indicative of the user's identity and the generated cardio-related physiologic data, as concerning the user associated with the scale-based biometric. The scale can receive user data from the other user devices and/or medical devices. In some embodiments, the scale authorizes the communication in response to a dual-authorization, such as receiving authorization data from the user device or medical device, as previously described.

In response to the authorization data, the user device and/or medical device collects signals, such as signals indicative of the cardio-physiologic data, exercise data, sleep data, and generates therefrom the user data. Further, the user device and/or medical device activates the communication by outputting the authorization data to the scale. Alternatively, the authorization data is output as a portion of the user data and the scale authorizes the data based on the authorization data.

At 134, the scale is modified based on treatment instructions received. For example, a healthcare professional provides the instructions, via circuitry communicating with the scale, and the scale is modified by storing the instructions. The scale can instruct the user, at 137, based on the treatment instructions. The instructions can include periodic indications that the user is not following the treatment plan, such as reminders that the user has dietary restrictions that are not being met.

At 144, the scale tracks user data from the scale and the user devices/medical devices over time, including changes to physiological parameters. Tracking the user data can include aggregating the user data from the user devices and medical devices with scale-obtained user data. In various embodiments, the aggregation includes the scale correlating and storing the data obtained by the user device, the medical device, and the scale with a user profile of the user. Further, at 146, the scale (or other CPU, such as a standalone CPU or server CPU in communication with the scale) identifies potential correlations to the changes to physiological parameters and other tracked data, such as changes in lifestyle habits, medication, and/or treatment.

At 141, the scale activates communication of the tracked data and, optionally, potential correlations to external circuitry 124 (FIG. 2). For example, the external circuitry 124 is accessible by the healthcare professional. The activation can include verifying authorization of the communication responsive to a scale-based biometric, as discussed above. At 142, the scale optionally secures the data. The scale outputs the user data, as aggregated, at 143 to external circuitry 124 in response to the authorization.

In a number of embodiments, the healthcare professional reviews the data and adjusts the treatment plan. For example, additional treatment instructions are sent to the scale and the scale is modified using the instructions responsive to a subsequent transition of the scale from the lower power mode, at 129, to the higher power mode, at 131, and validation that the user standing on the scale is the correct user at 132/133.

In various related embodiments, the tracked data and/or potential correlations are provided to the user. In some embodiments, the data is only provided after review by a physician. For example, the user is provided the potential correlation via the FUI of the scale and/or a GUI of one of the user devices such that the user visually sees changes to their physiological state caused by the treatment plan (or not following the treatment plan). Additional health information may be provided to the user to encourage the user to follow the treatment plan, such as risks or symptoms of their physiological state.

The system can include additional user devices and/or other body accessories and/or medical devices. Similarly, the scale can receive data from a plurality of user devices and/or other body accessories. In this way, the scale is used as a hub for collecting and correlating user data corresponding to a user. The scale collects the various data and correlates the data with a user profile corresponding with the user. The data from one of the user devices may conflict with data obtained by the scale. In such instances, the data obtained by the scale is used and the data from the user device is discarded. That is, the data from the scale is the default data as the scale may include greater processing resources and/or obtain higher quality signals than the user device.

Figure 4:
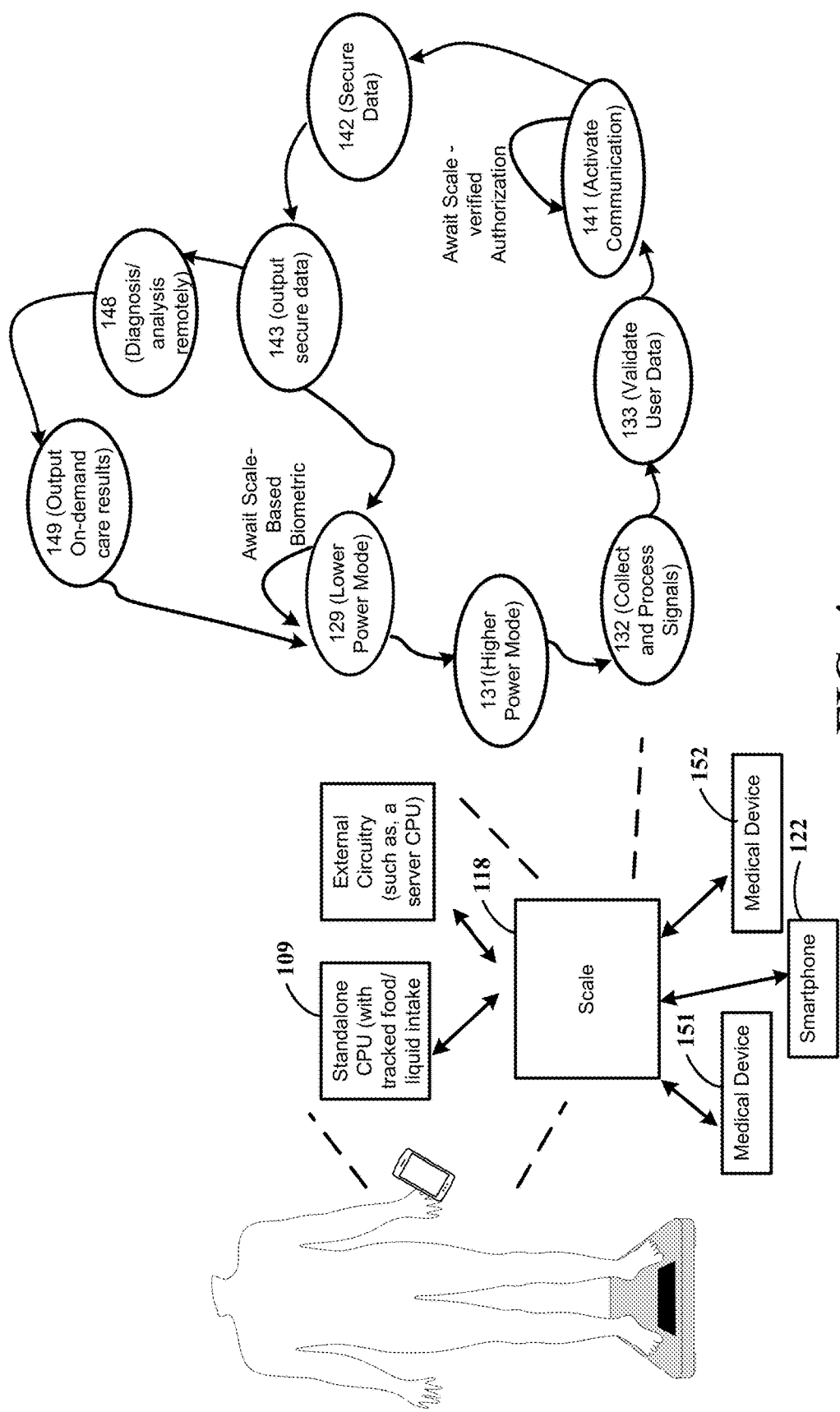
FIG. 4 shows an example of providing medical assessment of a user using a scale-based on-demand care system, consistent with aspects of the present disclosure.

FIG. 4 shows an example of providing medical assessment of a user, using a scale-based on-demand care system, consistent with aspects of the present disclosure. As illustrated the scale-based on-demand care system includes a scale 118, standalone CPU 109, and various user devices (e.g., smartwatch 121, smartphone 122, and smartcup 127 as labeled in FIG. 1c), and various medical devices 151, 152. The scale-based on-demand care system is used as a medical analytic driver that aggregates user data from the scale, the medical devices, and input by a healthcare professional from a test, and then filters the aggregated data based on trigger data (e.g., thresholds). The aggregated data is used to filter the Internet to provide potential diagnosis data, correlations, recommendations for additional tests and where to obtain the test(s), etc. The healthcare professional is provided the results from the filter, via the standalone CPU (and in some embodiments, from the external circuitry 124 of FIG. 2) and diagnose the user and/or otherwise provide recommendations, such as to visit a physician and/or a specialist.

The scale monitor signals and/or data indicative of physiologic parameters of the user while the user is standing on the platform (e.g., collect scale-based/obtained data). The user devices and/or medical devices further monitor signals and/or data indicative of physiologic parameters of the user. Both the scale and the user devices/medical devices collect user data of varying user sensitivities.

The standalone user CPU 109, and other user devices form a robust-GUI for the healthcare professional and/or the user to view various data. In some embodiments, the standalone user CPU 109 includes a personal computer, a laptop, a tablet, and/or a smartphone. Further, the scale 118 includes a GUI, such as a FUI. In various embodiments, using the scale-obtained data, such as user demographic data, various reports or dashboards are displayed using the FUI and/or the GUI. The reports/dashboards include displays of various scale-obtained parameter values and/or progress. As an example, a report is provided that illustrates the user's loss of weight from the last time a measurement was made by the scale. The user is given direct feedback and in some embodiments, visual indications, of their progress while having on-demand care. Additionally, the healthcare professional is provided with the report, which may contain additional detail, on the CPU 109 and/or other user devices.

As a specific example, a user is visiting a low-cost healthcare clinic and/or a traveling clinic. The user stands on the scale and in response, the scale transitions from a reduced power-consumption mode of operation at 129 to at least one higher power-consumption mode of operation at 131. At 132, the scale collects signals indicative of an identity of the user and cardio-physiological measurements (e.g., force signals) by engaging the user with electrical signals and, therefrom, collecting the signals. Further, at 132, the processing circuitry of the scale processes the signals obtained by the data-procurement circuitry while the user is standing on the platform and generates therefrom, cardio-related physiologic data corresponding to the collected signals.

At 133, the processing circuitry of the scale identifies a scale-based biometric of the user, using the collected signals and validates the user data, which includes the data indicative of the users' identity and the generated cardio-related physiologic data, as concerning the user associated with the scale-based biometric.

One or more of the medical devices and/or user devices may be unable to directly communicate with the scale. In such embodiments, the healthcare professional enters the data to the scale, such as to the standalone CPU 109 which communicates to the scale. As a particular example, the medical device 152 includes a blood-pressure device and/or a flu virus test that is not configured to communicate with other devices. The healthcare professional enters the results to the standalone CPU 109 via an application running on the CPU 109 and the CPU 109 communicates the data to the scale.

The user devices and medical devices, as previously discussed, include a device, including processing circuitry, configured to collect various signals from the user. In various embodiments, one or more of the devices are configured to operate in multiple modes. For example, the user device can wait for user authorization data from the user.

In various embodiments, the scale (and/or standalone CPU 109 or a server CPU) includes trigger data. The aggregated user data from the scale, the medical devices, and/or the user devices are compared to the trigger data to determine if the user has or is at risk for a condition, as previously discussed. In response to the trigger data and the aggregated user data indicating that the user has a risk for a condition, the scale and/or standalone user CPU 109 (or server CPU) filters the user data from the scale and the other user devices/medical devices 151, 152, 122 and filters data from the Internet and/or a research database to identify data that is relevant to the condition and/or recommendations for the user.

For example, first the user data is filtered to identify a subset of the user data that is relevant to the condition, such as based on the trigger data. The subset of user data and trigger data is used to filter data from the Internet, in various embodiments. The filter results in various additional health information identified by searching the Internet based on the filters, such as generic health information related to the condition, additional symptoms, additional tests or parameters to perform, devices and/or products related to the condition, blogs, studies, etc. In response to the filter identifying various health information related to a condition of the user, the results of the filter are provided to the healthcare professional for further review, analysis, and/or diagnosis purposes. For example, the healthcare professional further assesses the condition by viewing the various health information on the GUI of the standalone CPU 109.

In various embodiments, the on-demand care system includes use of external circuitry, such as a server CPU operated by an entity that provides on-demand diagnosis services. In such instances, the data is securely communicated. For example, at 141, the scale activates communication of the aggregated data to external circuitry 124 (operated by the entity). The activation can include verifying authorization of the communication responsive to a scale-based biometric, as discussed above. At 142, the scale secures the data. Securing the data includes various verification of the identity of the user (e.g., different biometrics to authorize different sensitivity levels), encryption schemes, software keys, hardware token keys, among other techniques. The scale outputs the user data, as aggregated, at 143 to the external circuitry 124 in response to the authorization and security. The entity, at 148, further processes the aggregated data remotely and/or for diagnosis purposes and, at 149, outputs on-demand care results back to the scale for the healthcare professional to review.

The on-demand care results provided remotely can include recommended diagnosis and explanation for the diagnosis, recommended treatments, recommendations to see a specialist and/or have additional tests performed, etc. In some embodiments, the on-demand care results (e.g., diagnosis) is reviewed and/or determined by a licensed physician and the results are provided to the patient by a healthcare professional that is not a licensed physician, such as a nurse. Thereby, using the system, the nurse is able to provide care, including prescriptions and diagnosis, using a remote physician. In other embodiments, the healthcare professional is a licensed physician and/or can provide limited service due to local regulations (even if the data is remotely analyzed by a licensed physician). For example, some States may not allow for remote diagnosis of patients by a licensed physician. In such cases, the nurse is able to recommend that a user visit a physician in response to the data indicating a condition and, optionally, responsive to user authorization, forwards the results to the respective physician in advance of the visit (or provide the data to the user). Thereby, the scale is used as part of an on-demand care system used to lower the cost of providing healthcare services, increase the number of patients that can be seen in a day, allow for care to be provided in remote locations, and/or potentially reduce unneeded physician visits.

The FUI of the scale can be used to provide portions of the user data, on-demand care results, generic health information, and/or other feedback to the user. In some embodiments, the scale includes a display configuration filter (e.g., circuitry and/or computer readable medium) that discerns the data to display to the user and displays the portion. The display configuration filter discerns which portions of the data to display to the user on the FUI based on various user demographic information (e.g., age, gender, height, diagnosis) and the amount of data. For example, the generic health information identified from the filter may include an amount of data that if all the data is displayed on the foot-controlled user interface, the data is difficult for a person to read and/or uses multiple display screens.

The display configuration filter discerns portions of the data to display using the scale user interface, such as synopsis of the generic health information (or user data or feedback) and an indication that additional data is displayed on another user device, and other portions to display on the other user device (e.g., the smartphone 122). The other user device is selected by the scale (e.g., the filter) based on various communication settings. The communication settings include settings such as user settings (e.g., the user identifying user devices to output data to), scale-based biometrics (e.g., user configures scale, or default settings, to output data to user devices in response to identifying scale-based biometrics), and/or proximity of the user device (e.g., the scale outputs data to the closest user device among a plurality of user devices and/or in response to the user device being within a threshold distance from the scale), among other settings. For example, the scale determines which portions of the user data, generic health information and/or other feedback to output and outputs the remaining portion of the user data, generic health information and/or other feedback to a particular user device based on user settings/communication authorization (e.g., what user devices are authorized by the user to receive particular user data from the scale), and proximity of the user device to the scale. The determination of which portions to output is based on what type of data is being displayed, how much data is available, and the various user demographic information (e.g., an eighteen year old is able to see better than a fifty year old).

The remaining figures illustrate various ways to collect the physiologic data from the user, electrode configurations, and alternative modes of the processing circuitry 104. For general and specific information regarding the collection of physiologic data, electrode configurations, and alternative modes, reference is made to U.S. patent application Ser. No. 14/338,266 filed on Oct. 7, 2015 (now U.S. Pat. No. 10,130, 273), which is hereby fully incorporated by references for its teachings.

Figure 5:
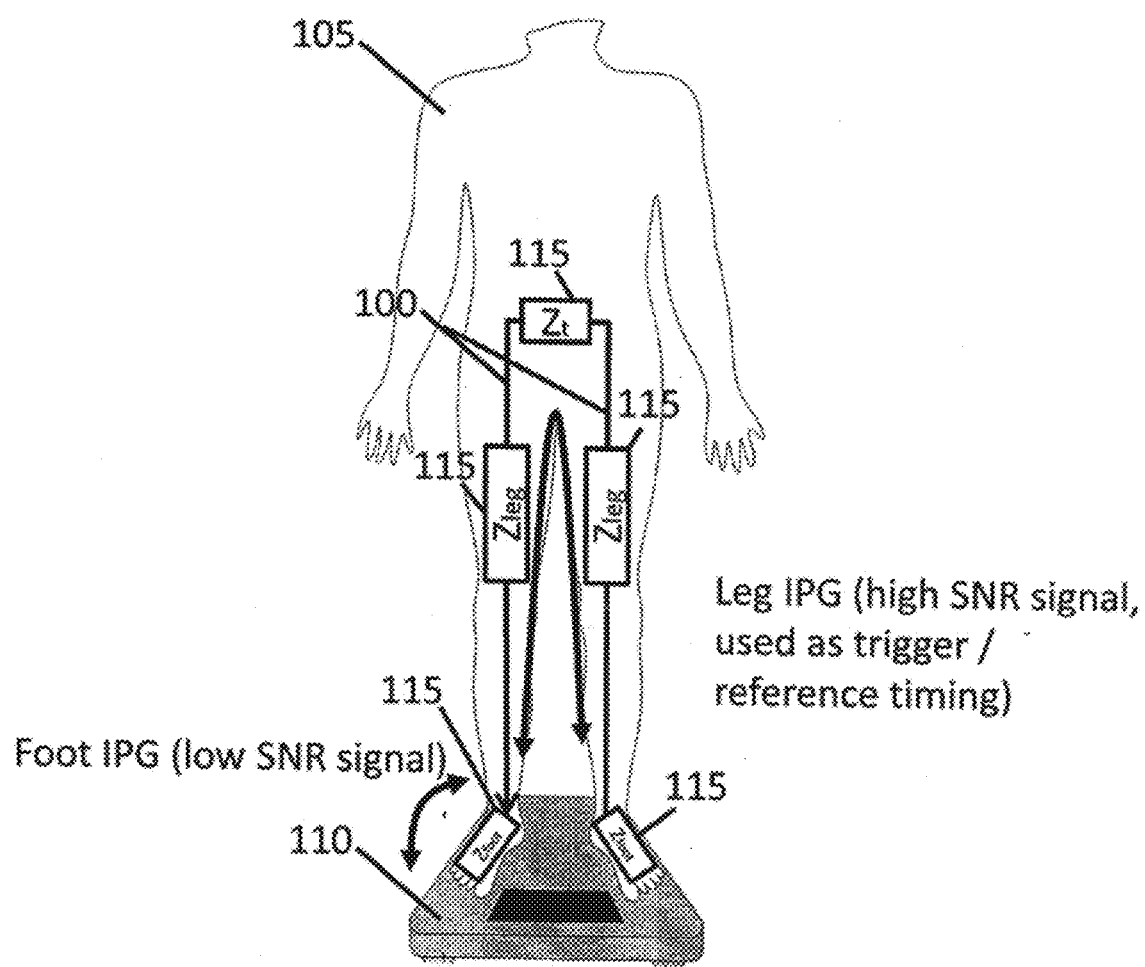
FIG. 5 shows current paths through the body for the IPG trigger pulse and Foot IPG, consistent with various aspects of the present disclosure.

FIG. 5 shows current paths 100 through the body of a user 105 standing on a scale 110 for the IPG trigger pulse and Foot IPG, consistent with various aspects of the present disclosure. Impedance measurements 115 are measured when the user 105 is standing and wearing clothing articles over the feet (e.g., socks or shoes), within the practical limitations of capacitive-based impedance sensing, with energy limits considered safe for human use. The measurements 115 can be made with non-clothing material placed between the user's bare feet and contact electrodes, such as thin films or sheets of plastic, glass, paper or wax paper, whereby the electrodes operate within energy limits considered safe for human use. The IPG measurements can be sensed in the presence of callouses on the user's feet that normally diminish the quality of the signal.

As shown in FIG. 5, the user 105 is standing on a scale 110, where the tissues of the user's body will be modeled as a series of impedance elements, and where the time-varying impedance elements change in response to cardiovascular and non-cardiovascular movements of the user. ECG and IPG measurements sensed through the feet can be challenging to take due to small impedance signals with (1) low SNR, and because they are (2) frequently masked or distorted by other electrical activity in the body such as the muscle firings in the legs to maintain balance. The human body is unsteady while standing still, and constant changes in weight distribution occur to maintain balance. As such, cardiovascular signals that are measured with weighing scale-based sensors typically yield signals with poor SNR, such as the Foot IPG and standing BCG. Thus, such scale-based signals require a stable and high quality synchronous timing reference, to segment individual heartbeat-related signals for signal averaging to yield an averaged signal with higher SNR versus respective individual measurements.

The ECG can be used as the reference (or trigger) signal to segment a series of heartbeat-related signals measured by secondary sensors (optical, electrical, magnetic, pressure, microwave, piezo, etc.) for averaging a series of heartbeat-related signals together, to improve the SNR of the secondary measurement. The ECG has an intrinsically high SNR when measured with body-worn gel electrodes, or via dry electrodes on handgrip sensors. In contrast, the ECG has a low SNR when measured using foot electrodes while standing on said scale platforms; unless the user is standing perfectly still to eliminate electrical noises from the leg muscles firing due to body motion. As such, ECG measurements at the feet while standing are considered to be an unreliable trigger signal (low SNR). Therefore, it is often difficult to obtain a reliable cardiovascular trigger reference timing when using ECG sensors incorporated in base scale platform devices. Both Inan, et al. (IEEE Transactions on Information Technology in Biomedicine, 14:5, 1188-1196, 2010) and Shin, et al. (Physiological Measurement, 30, 679-693, 2009) have shown that the ECG component of the electrical signal measured between the two feet while standing was rapidly overpowered by the electromyogram (EMG) signal resulting from the leg muscle activity involved in maintaining balance.

The accuracy of cardiovascular information obtained from weighing scales is also influenced by measurement time. The number of beats obtained from heartbeats for signal averaging is a function of measurement time and heart rate. Typically, a resting heart rate ranges from 60 to 100 beats per minute. Therefore, short signal acquisition periods may yield a low number of beats to average, which may cause measurement uncertainty, also known as the standard error in the mean (SEM). SEM is the standard deviation of the sample mean estimate of a population mean. Where, SE is the standard error in the samples N, which is related to the standard error or the population S.

$$SE = S/\sqrt{N}$$

For example, a five second signal acquisition period may yield a maximum of five to eight beats for ensemble averaging, while a 10 second signal acquisition could yield 10-16 beats. However, the number of beats available for averaging and SNR determination is usually reduced for the following factors; (1) truncation of the first and last ensemble beat in the recording by the algorithm, (2) triggering beats falsely missed by triggering algorithm, (3) cardiorespiratory variability, (4) excessive body motion corrupting the trigger and Foot IPG signal, and (5) loss of foot contact with the measurement electrodes.

Sources of noise can require multiple solutions for SNR improvements for the signal being averaged. Longer measurement times increase the number of beats lost to truncation, false missed triggering, and excessive motion. Longer measurement times also reduce variability from cardiorespiratory effects. If shorter measurement times (e.g., less than 30 seconds) are desired for scale-based sensor platforms, sensing improvements need to tolerate body motion and loss of foot contact with the measurement electrodes.

Surprisingly, high quality simultaneous recordings of the Leg IPG and Foot IPG are attainable in a practical manner (e.g., a user operating the device correctly simply by standing on the impedance body scale foot electrodes), and can be used to obtain reliable trigger fiducial timings from the Leg IPG signal. This acquisition can be far less sensitive to motion-induced noise from the Leg EMG that often compromises Leg ECG measurements. Furthermore, it has been discovered that interleaving the two Kelvin electrode pairs for a single foot, result in a design that is insensitive to foot placement within the boundaries of the overall electrode area. As such, the user is not constrained to comply with accurate foot placement on conventional single foot Kelvin arrangements, which are highly prone to introducing motion artifacts into the IPG signal, or result in a loss of contact if the foot is slightly misaligned. Interleaved designs begin when one or more electrode surfaces cross over a single imaginary boundary line separating an excitation and sensing electrode pair. The interleaving is configured to maintain uniform foot surface contact area on the excitation and sensing electrode pair, regardless of the positioning of the foot over the combined area of the electrode pair.

Various aspects of the present disclosure include a weighing scale platform (e.g., scale 110) of an area sufficient for an adult of average size to stand comfortably still and minimize postural swaying. The nominal scale length (same orientation as foot length) is 12 inches and the width is 12 inches. The width can be increased to be consistent with the feet at shoulder width or slightly broader (e.g., 14 to 18 inches, respectively).

Figure 6:
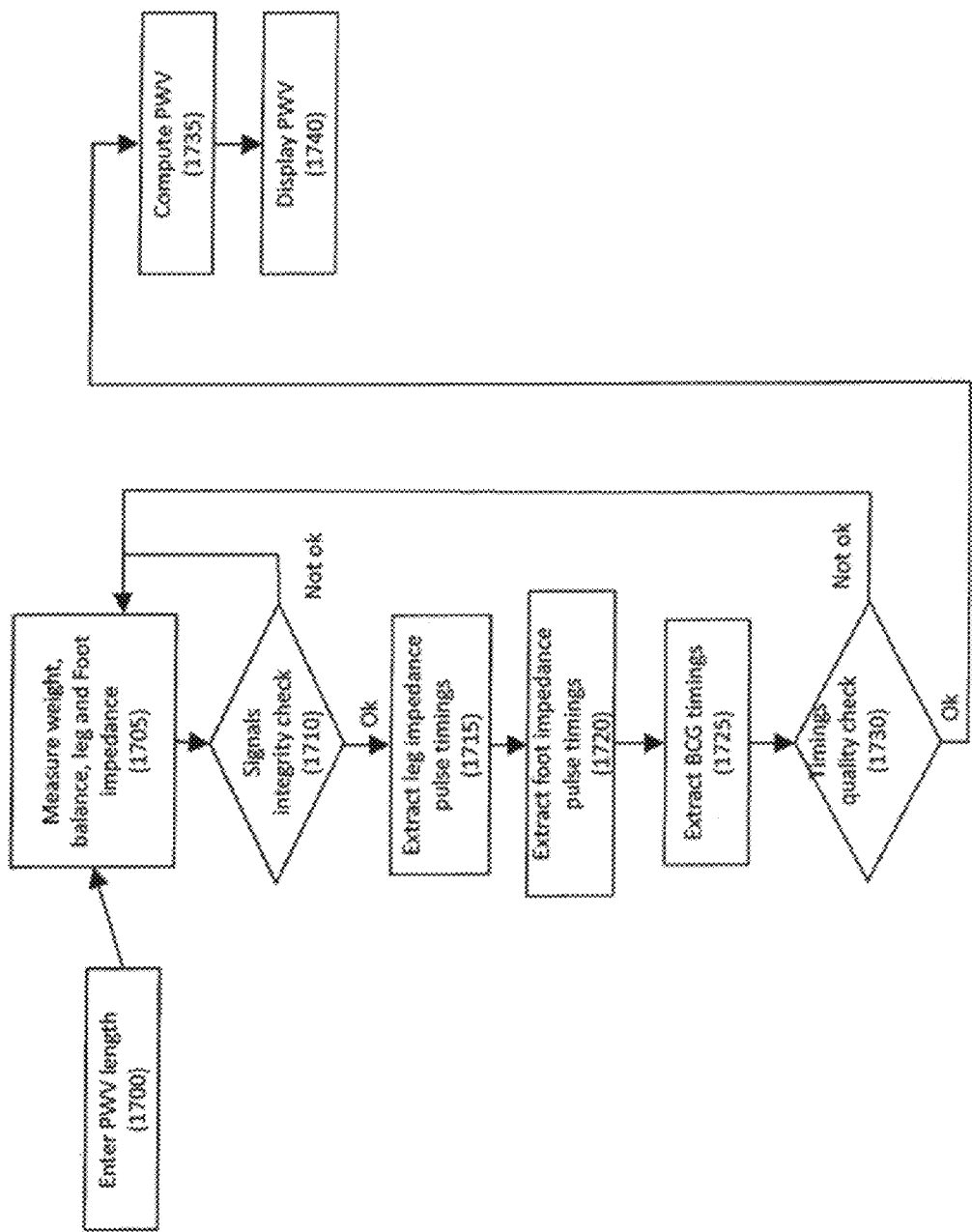
FIG. 6 shows an example flow diagram, consistent with various aspects of the present disclosure.

FIG. 6 shows an example flow diagram, consistent with various aspects of the present disclosure. At block 1700, a PWV length is entered. At block 1705, a user's weight, balance, leg, and foot impedance are measured. At 1710, the integrity of signals is checked (e.g., SNR). If the signal integrity check is not met, the user's weight, balance, leg, and foot impedance are measured again (block 1705), if the signals integrity check is met, the leg impedance pulse timings are extracted (as is shown at block 1715). At block 1720, foot impedance and pulse timings are extracted, and at block 1725, BCG timings are extracted. At block 1730, a timings quality check is performed. If the timings quality check is not validated, the user's weight, balance, leg and foot impedance are again measured (block 1705). If the timings quality check is validated, the PWV is calculated (as is shown at block 1735). At block 1740, the PWV is displayed to the user.

Figure 7:
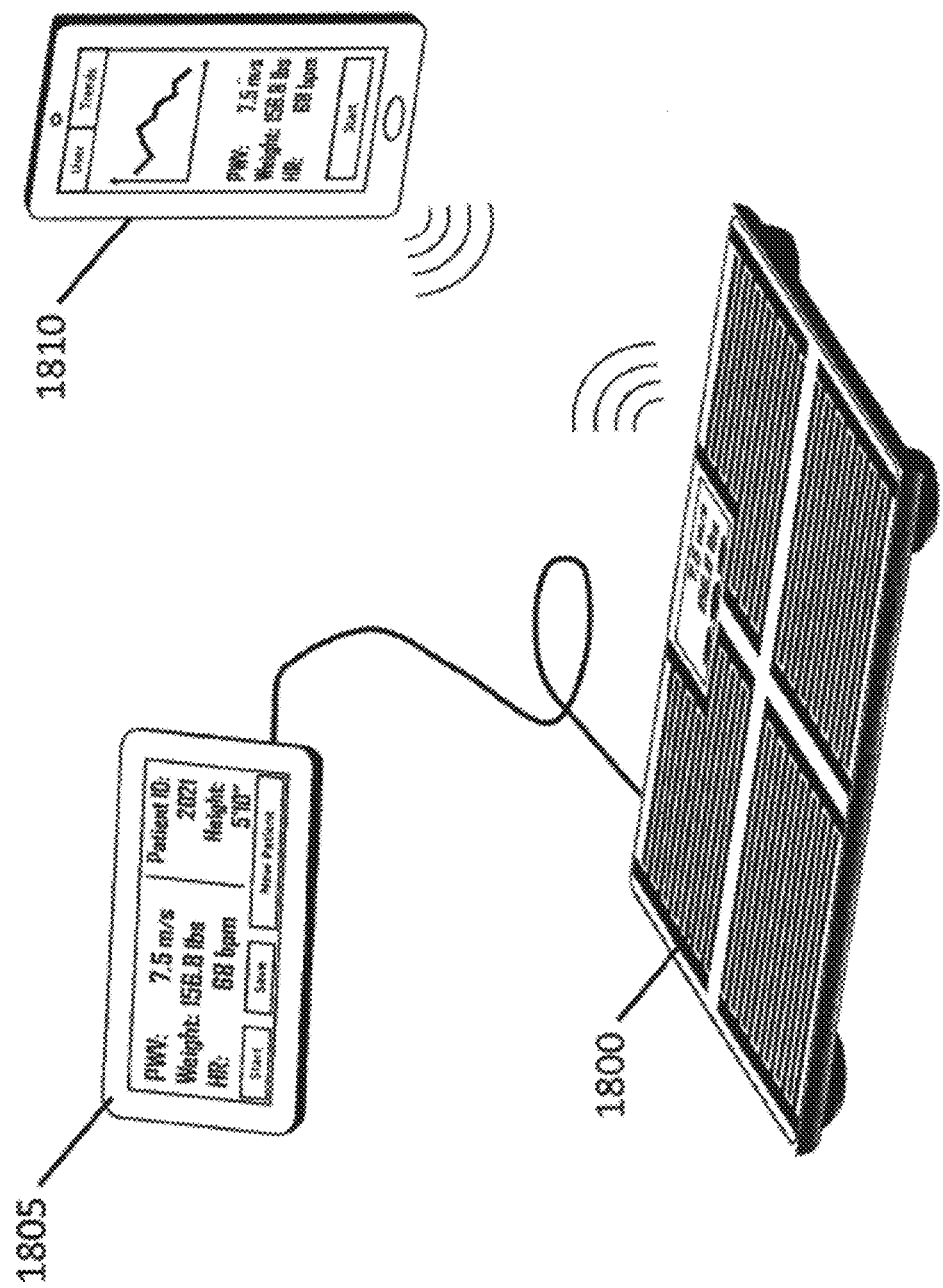
FIG. 7 shows an example scale communicatively coupled to a wireless device, consistent with various aspects of the present disclosure.

FIG. 7 shows an example scale 1800 communicatively coupled to a wireless device, consistent with various aspects of the present disclosure. As described herein, a display 1805 displays the various aspects measured by the scale 1800. The scale, in some embodiments, also wirelessly broadcast the measurements to a wireless device 1810. The wireless device 1810, in various embodiments, is implemented as an iPad®, smart phone or other CPU to provide input data for configuring and operating the scale.

As an alternative or complementary user interface, the scale includes a foot-controlled user interface which can be enabled/implementable by one or more foot-based biometrics (for example, with the user being correlated to previously-entered user weight, and/or foot size/shape). The user foot-based biometric, in some embodiments, is implemented by the user manually entering data (e.g., a password) on the upper surface or display area of the scale. In implementations in which the scale is configured with a haptic, capacitive or flexible pressure-sensing upper surface, the (upper surface/tapping) touching from or by the user is sensed in the region of the surface and processed according to conventional X-Y grid Signal processing in the logic circuitry/CPU that is within the scale. By using one or more of the accelerometers located within the scale at its corners, such user data entry is sensed by each such accelerometer so long as the user's toe, heel or foot pressure associated with each tap provides sufficient force.

Figure 8A:
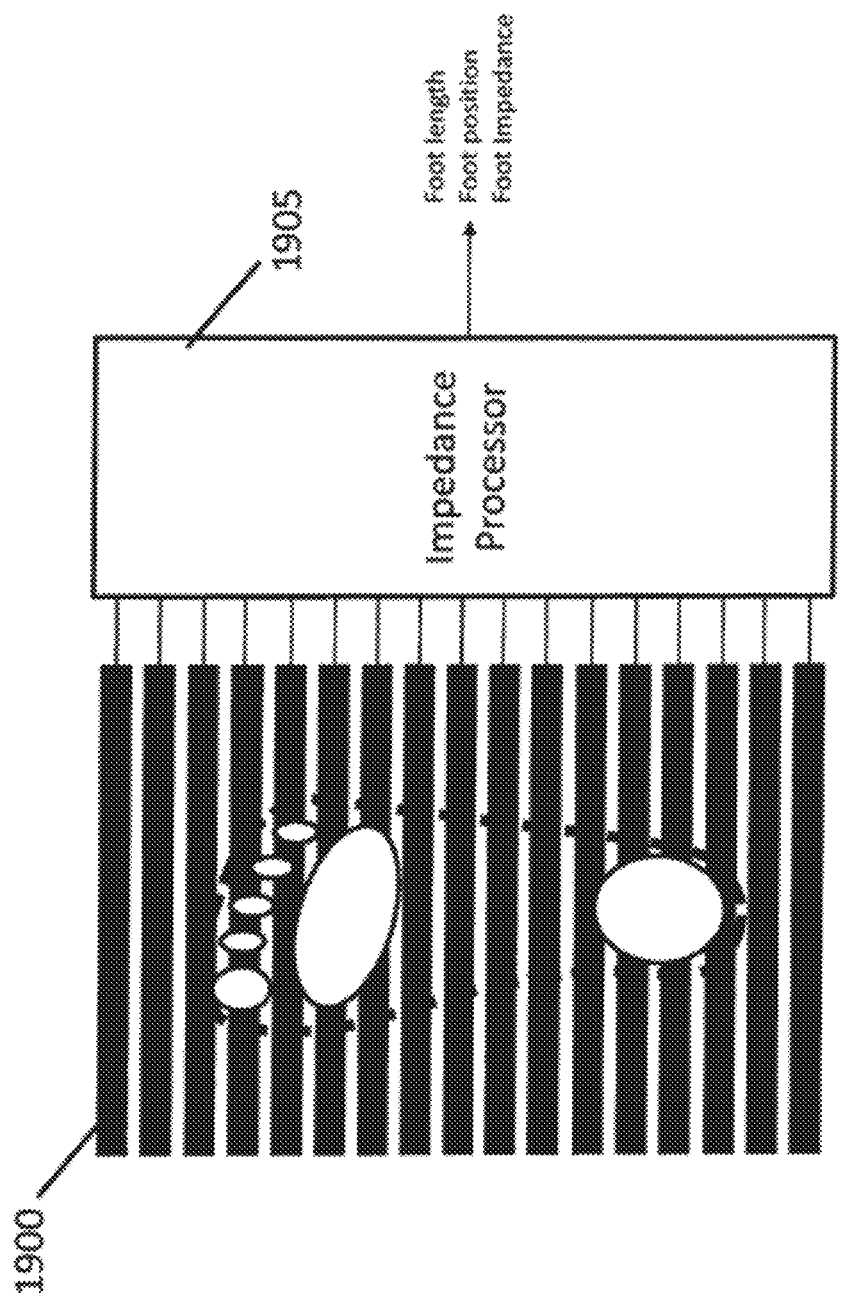
FIGS. 8A-8C show example impedance as measured through different parts of the foot based on the foot position, consistent with various aspects of the present disclosure.
Figure 8B:
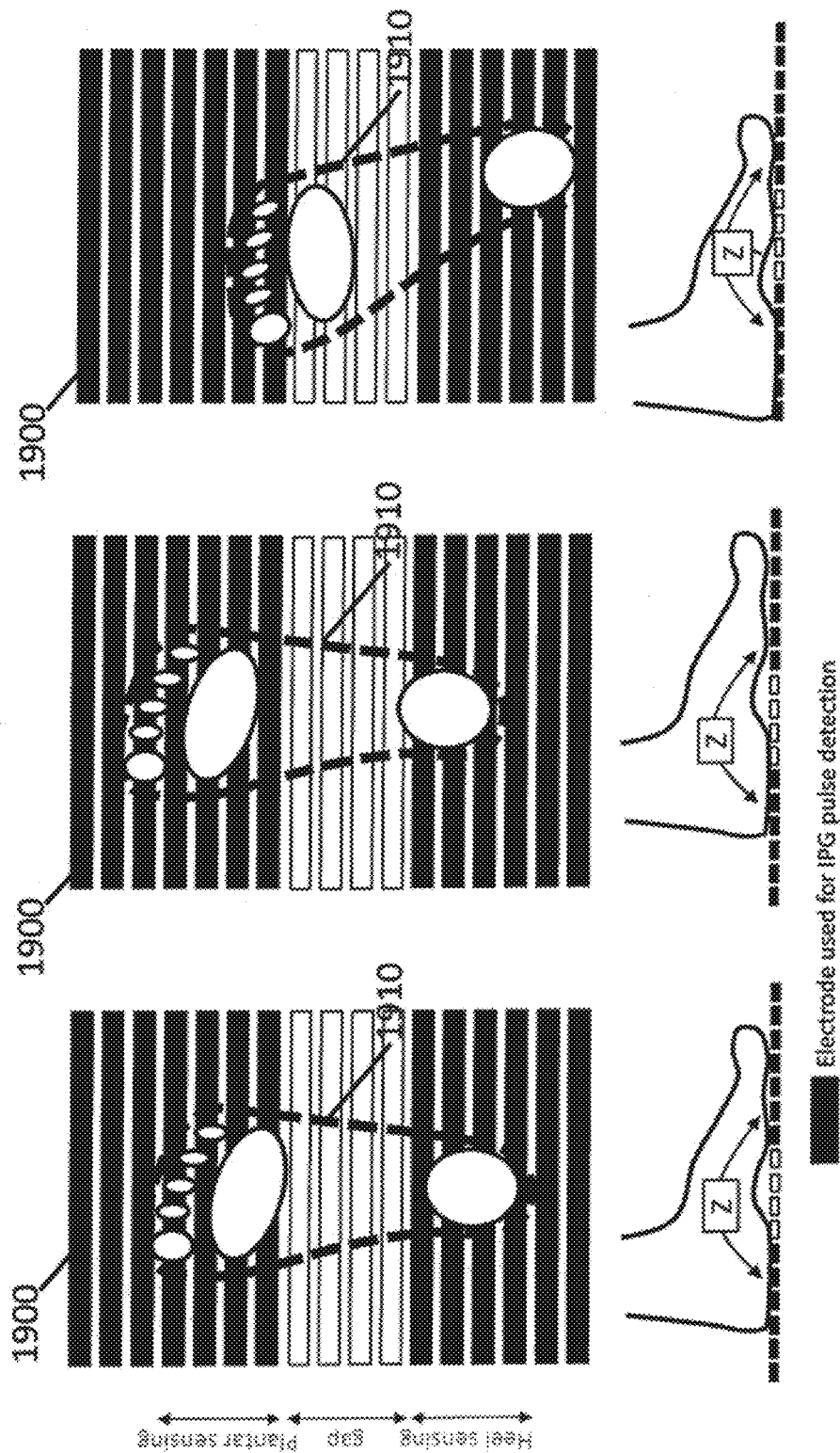
Figure 8C:
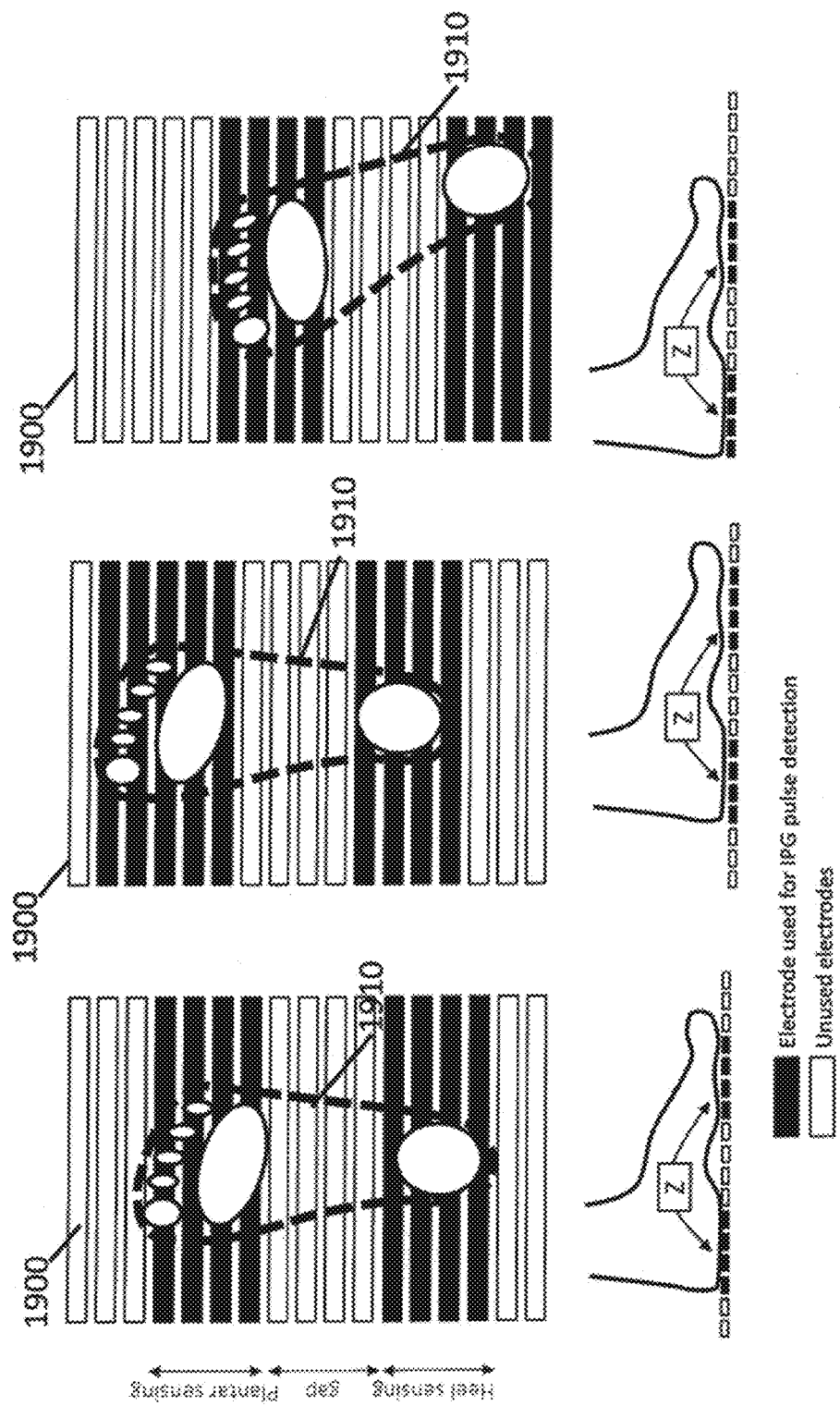

FIGS. 8A-C show example impedance as measured through different parts of the foot based on the foot position, consistent with various aspects of the present disclosure. For instance, example impedance measurement configurations may be implemented using a dynamic electrode configuration for measurement of foot impedance and related timings. Dynamic electrode configuration may be implemented using independently-configurable electrodes to optimize the impedance measurement. As shown in FIG. 8A, interleaved electrodes 1900 are connected to an impedance processor circuit 1905 to determine foot length, foot position, and/or foot impedance. As is shown in FIG. 8B, an impedance measurement is determined regardless of foot position 1910 based on measurement of the placement of the foot across the electrodes 1900. This is based in part in the electrodes

1900 that are engaged (blackened) and in contact with the foot (based on the foot position 1910), which is shown in FIG. 8C.

More specifically regarding FIG. 8A, configuration includes connection/de-connection of the individual electrodes 1900 to the impedance processor circuit 1905, their configuration as current-carrying electrodes (injection or return), sense electrodes (positive or negative), or both. The configuration is preset based on user information, or updated at each measurement (dynamic reconfiguration) to optimize a given parameter (impedance SNR, measurement location). The system algorithmically determines which electrodes under the foot to use in order to obtain the highest SNR in the pulse impedance signal. Such optimization algorithm may include iteratively switching configurations and measuring the impedance, and selecting the best suited configuration. Alternatively, the system first, through a sequential impedance measurement between each individual electrode 1900 and another electrode in contact with the body (such as an electrode in electrode pair 205 on the other foot), determine which electrodes are in contact with the foot. By determining the two most apart electrodes, the foot size is determined. Heel location can be determined in this manner, as can other characteristics such as foot arch type. These parameters are used to determine programmatically (in an automated manner by CPU/logic circuitry) which electrodes are selected for current injection and return (and sensing if a Kelvin connection issued) to obtain the best foot IPG.

In various embodiments involving the dynamically reconfigurable electrode array 1900/1905, an electrode array set is selected to measure the same portion/segment of the foot, irrespective of the foot location on the array. FIG. 8B illustrates the case of several foot positions on a static array (a fixed set of electrodes are used for measurement at the heel and plantar/toe areas, with a fixed gap of an inactive electrode or insulating material between them). Depending on the position of the foot, the active electrodes are contacting the foot at different locations, thereby sensing a different volume/segment of the foot. If the IPG is used by itself (e.g., for heart measurement), such discrepancies may be non-consequential. However, if timings derived from the IPG are referred to other timings (e.g., R-wave from the ECG, or specific timing in the BCG), such as for the calculation of a PTT or PWV, the small shifts in IPG timings due to the sensing of slightly different volumes in the foot (e.g., if the foot is not always placed at the same position on the electrodes) can introduce an error in the calculation of the interval. With respect to FIG. 8B, the timing of the peak of the IPG from the foot placement on the right (sensing the toe/plantar region) is later than from the foot placement on the left, which senses more of the heel volume (the pulse reaches first the heel, then the plantar region). Factors influencing the magnitude of these discrepancies include foot shape (flat or not) and foot length.

Various embodiments address challenges relating to foot placement. FIG. 8C shows an example embodiment involving dynamic reconfiguration of the electrodes to reduce such foot placement-induced variations. As an example, by sensing the location of the heel first (as described above), it is possible to activate a subset of electrodes under the heel, and another subset of electrodes separated by a fixed distance (1900). The other electrodes (e.g., unused electrodes) are left disconnected. The sensed volume will therefore be the same, producing consistent timings. The electrode configuration leading to the most consistent results may be informed by the foot impedance, foot length, the type of arch (all of which can be measured by the electrode array as shown above), but also by the user ID (foot information can be stored for each user, then looked up based on automatic user recognition or manual selection (e.g., in a look-up-table stored for each user in a memory circuit accessible by the CPU circuit in the scale).

In certain embodiments, the apparatus measures impedance using a plurality of electrodes contacting one foot and with at least one other electrode (typically many) at a location distal from the foot. The plurality of electrodes (contacting the one foot) is arranged on the platform and in a pattern configured to inject current signals and sense signals in response thereto, for the same segment of the foot so that the timing of the pulse-based measurements does not vary because the user placed the one foot at a slightly different position on the platform or scale. In FIG. 8A, the foot-to-electrode locations for the heel are different locations than that shown in FIGS. 8B and 8C. As this different foot placement can occur from day to day for the user, the timing and related impedance measurements are for the same (internal) segment of the foot. By having the processor circuit inject current and sense responsive signals to first locate the foot on the electrodes (e.g., sensing where positions of the foot's heel plantar regions and/or toes), the pattern of foot-to-electrode locations permits the foot to move laterally, horizontally and both laterally and horizontally via the different electrode locations, while collecting impedance measurements relative to the same segment of the foot.

The BCG/IPG system can be used to determine the PTT of the user, by identification of the average I-Wave or derivative timing near the I-Wave from a plurality of BCG heartbeat signals obtained simultaneously with the Dual-IPG measurements of the present disclosure to determine the relative PTT along an arterial segment between the ascending aortic arch and distal pulse timing of the user's lower extremity. In certain embodiments, the BCG/IPG system is used to determine the PWV of the user, by identification of the characteristic length representing the length of the user's arteries, and by identification of the average I-Wave or derivative timing near the I-Wave from a plurality of BCG heartbeat signals obtained simultaneously with the Dual-IPG measurements of the present disclosure to determine the relative PTT along an arterial segment between the ascending aortic arch and distal pulse timing of the user's lower extremity. The system of the present disclosure and alternate embodiments may be suitable for determining the arterial stiffness (or arterial compliance) and/or cardiovascular risk of the user regardless of the position of the user's feet within the bounds of the interleaved electrodes. In certain embodiments, the weighing scale system incorporated the use of strain gage load cells and six or eight electrodes to measure a plurality of signals including: bodyweight, BCG, body mass index, fat percentage, muscle mass percentage, and body water percentage, heart rate, heart rate variability, PTT, and PWV measured simultaneously or synchronously when the user stands on the scale to provide a comprehensive analysis of the health and wellness of the user.

In other certain embodiments, the PTT and PWV are computed using timings from the Leg IPG or Foot IPG for arrival times, and using timings from a sensor located on the upper body (as opposed to the scale measuring the BCG) to detect the start of the pulse. Such sensor may include an impedance sensor for impedance cardiography, a hand-to-hand impedance sensor, a photoplethysmogram on the chest, neck, head, arms or hands, or an accelerometer on the chest (seismocardiograph) or head.

Communication of the biometric information is another aspect of the present disclosure. The biometric results from the user are stored in the memory on the scale and displayed to the user via a display on the scale, audible communication from the scale, and/or the data is communicated to a peripheral device such as a computer, smart phone, and/or tablet computing device. The communication occurs to the peripheral device with a wired connection, or can be sent to the peripheral device through wireless communication protocols such as Bluetooth or WiFi. Computations such as signal analyses described therein may be carried out locally on the scale, in a smartphone or computer, or in a remote processor (cloud computing).

Other aspects of the present disclosure are directed toward apparatuses or methods that include the use of at least two electrodes that contacts feet of a user. Further, circuitry is provided to determine a pulse arrival time at the foot based on the recording of two or more impedance signals from the set of electrodes. Additionally, a second set of circuitry is provided to extract a first pulse arrival time from a first impedance signal and use the first pulse arrival time as a timing reference to extract and process a second pulse arrival time in a second impedance signal.

Various embodiments are implemented in accordance with the underlying Provisional Application (Ser. No. 62/331,655) filed on May 4, 2016 and entitled "Scale-Based On-Demand Care System" to which benefit is claimed and is fully incorporated herein by reference. For instance, embodiments herein and/or in the provisional application (including the appendices therein) may be combined in varying degrees (including wholly). For information regarding details of these and other embodiments, applications and experiments (as combinable in varying degrees with the teachings herein), reference may be made to the teachings and underlying references provided in the Provisional Applications and which forms part of this patent document and is fully incorporated herein. Accordingly, the present disclosure is related to methods, applications and devices in and stemming from the disclosures provisional (including the references and illustrations therein), and also to the uses and development of devices and processes discussed in connection with the references cited herein.

For further discussion of aspects and features combinable with the above embodiments, reference may be made to the underlying provisional patent application (Ser. No. 62/331, 655) and to the related teaching in one or more of the below-listed US Letters Patents (each being incorporated by reference) as follows: manner in which a user-specific physiologic meter/scale may be programmed to provide features as in FIG. 1*f,* insensitivity to foot placement on scale electrodes with multiple excitation and sensing current paths as in FIG. 2, depicting circuitry for sensing and measuring cardiovascular time-varying IPG raw signals and steps to obtain a filtered IPG waveform as in FIGS. 3*a*-3*d,* depicting signal processing steps to obtain fiducial references from the individual Leg IPG "beats," as in FIG. 4, depicting signal processing to segment individual Foot IPG "beats" to produce an averaged IPG waveform of improved SNR, as in FIG. 5, examples of the leg IPG signal with fiducials, as in FIGS. 6*a,* 6*b,* 7*a,* and 7*b,* example correlation plots for the reliability in obtaining the low SNR Foot IPG pulse, as in FIG. 8, example configuration to obtain the pulse transit time (PTT), as in FIGS. 9*a*-9*b,* nomenclature and relationships of various cardiovascular timings, as in FIG. 10, an example graph of PTT correlations for two detection methods, as in FIG. 11, an example graph of pulse wave velocity, as in FIG. 12, a scale with interleaved foot electrodes, as in FIG. 13 and FIGS. 14*a*-14*c,* example breakdown of a scale with interleaved foot electrodes, as in FIGS. 15*a*-15-*c,* and circuit-based building blocks, as in FIG. 16 of the underlying provisional patent application; systems and methods for detecting heart function and processing signals therefore, see U.S. Pat. No. 8,870,780; and obtaining pulse wave velocity using such multiple scale electrodes, see U.S. Pat. No. 9,011,346.

Reference may also be made to published patent documents U.S. Patent Publication 2010/0094147 and U.S. Patent Publication 2013/0310700, which are, together with the references cited therein, herein fully incorporated by reference for the purposes of sensors and sensing technology. The aspects discussed therein may be implemented in connection with one or more of embodiments and implementations of the present disclosure (as well as with those shown in the figures). In view of the description herein, those skilled in the art will recognize that many changes may be made thereto without departing from the spirit and scope of the present disclosure.

As illustrated herein, various circuit-based blocks and/or modules may be implemented to carry out one or more of the operations/activities described herein shown in the block-diagram-type figures. In such contexts, these blocks and/or modules represent circuits that carry out these or related operations/activities. For example, in certain embodiments, one or more blocks/modules are discrete logic circuits or programmable logic circuits for implementing these operations/activities, as in the circuit blocks/modules shown. In certain embodiments, the programmable circuit is one or more computer circuits programmed to execute a set (or sets) of instructions (and/or configuration data). The instructions (and/or configuration data) can be in the form of firmware or software stored in and accessible from a memory circuit. As an example, first and second modules/blocks include a combination of a CPU hardware-based circuit and a set of instructions in the form of firmware, where the first module/block includes a first CPU hardware circuit with one set of instructions and the second module/block includes a second CPU hardware circuit with another set of instructions.

Based upon the above discussion and illustrations, those skilled in the art will readily recognize that various modifications and changes may be made to the present disclosure without strictly following the exemplary embodiments and applications illustrated and described herein. For example, the input terminals as shown and discussed may be replaced with terminals of different arrangements, and different types and numbers of input configurations (e.g., involving different types of input circuits and related connectivity). Such modifications do not depart from the true spirit and scope of the present disclosure, including that set forth in the following claims.

What is claimed is:

1. An apparatus for use with a plurality of user devices, each the plurality of user devices including circuitry to collect and to communicate user-specific physiological data, the apparatus comprising:

a weighing scale platform configured to support a standing user and to include circuitry having a plurality of sensors, the plurality of sensors being configured and arranged to engage the user and in response, collect cardiovascular data from the user including information indicative of heart rate; and processing circuitry including a CPU and a memory circuit configured and arranged under the platform upon which the user stands and in communication with the circuitry and with at least one of the plurality of user devices and to receive both the collected user-specific physiological data and the collected cardiovascular data, wherein the processing circuitry authorizes communication by the weighing scale platform with the one or more of the user devices and in response to the authorization receives the collected user-specific physiological data from the at least one user device;

the processing circuitry being configured and arranged to aggregate the collected user-specific physiological data and the collected cardiovascular data and in response generate aggregated user-specific data for reporting whether the aggregated user-specific data corresponds to a health condition by the processing circuitry accessing a database or a computer network and searching whether information concerning the aggregated data and matches criteria for triggering an alert of the health condition, and sending a report or an alert to display circuitry which is configured and arranged to alert the user or a healthcare professional.

2. The apparatus of claim 1, further including the at least one of the plurality of user devices, wherein the at least one user device is configured and arranged to provide authorization data to the processing circuitry for authorizing the communication with the weighing scale platform.

3. The apparatus of claim 1, wherein the processing circuitry is further configured and arranged to determine a PTT (pulse transit time) or a PWV (pulse wave velocity) of the user-based timings from another sensor engaging an upper body portion of the user, wherein PTT timing data is obtained from the weighing scale platform and from another user location.

4. The apparatus of claim 1, wherein the processing circuitry is further configured and arranged to determine a PTT (pulse transit time) or a PWV (pulse wave velocity) of the user-based timings from an impedance sensor engaging an upper body portion of the user from hand to hand.

5. The apparatus of claim 1, wherein the processing circuitry is further configured and arranged to determine a PTT (pulse transit time) or a PWV (pulse wave velocity) of the user-based timings from an impedance sensor engaging an upper body portion of the user as a photoplethysmogram on the chest, neck, head, arms or hands.

6. The apparatus of claim 1, wherein the processing circuitry is further configured and arranged to obtain from the user further cardiovascular-specific data, and use as part of the aggregated data: user data concerning activity indicated by an accelerometer, and user data from an impedance measurement obtained by using at least one electrode contacting one foot of the user and at least one other electrode contacting another location of the user which is distal from the one foot.

7. The apparatus of claim 1, wherein the processing circuitry is further configured and arranged to obtain from the user further cardiovascular-specific data provided by an impedance sensor which is configured and arranged to engage the user at the chest, and use as part of the aggregated data, data that is provided by the impedance sensor.

8. The apparatus of claim 1, wherein the processing circuitry is further configured and arranged to collect other user data from others of the plurality of user devices, the other user data including at least one of exercise data, sleep data and dietary tracking data, wherein prior to collecting the other user data, the processing circuitry authorizes communication with each of the plurality of the user devices using authorization data provided by the plurality of user devices, the authorization data being selected from the group consisting of a password, a passcode, a biometric, a cellphone identification, and combination thereof.

9. The apparatus of claim 1, wherein the processing circuitry is further configured and arranged to determine arterial stiffness or compliance.

10. The apparatus of claim 1, wherein the processing circuitry is further configured and arranged to process and use cardiogram data for the aggregate data, and wherein the health condition is based in part on demographic information and weight information, each corresponding to the user.

11. An apparatus for use with a plurality of user devices, each the plurality of user devices including circuitry to collect and to communicate user data, the apparatus comprising:

a weighing scale including:

a platform in which a plurality of sensors are integrated and configured and arranged for engaging a user; and processing circuitry including a CPU and a memory circuit configured and arranged under the platform upon which the user stands, wherein at least some of the processing circuitry is electrically integrated with the plurality of sensors under the platform and configured to collect physiological data from the user by:

authorizing communication by the weighing scale platform with the plurality of user devices and/or medical devices and, in response to the authorization, receives the user data from the plurality of user devices and/or medical devices;

aggregating scale-obtained data collected from the user while the user is standing on the platform with the user data from the plurality of user devices and/or medical devices;

filtering a database or a system of computer networks with the aggregated data in response to the aggregated data matching trigger data indicating the user is at risk for a health condition; and providing the aggregated data and filtered data to external circuitry accessible by a healthcare professional for review and for providing on-demand care.

12. The apparatus of claim 11, wherein the processing circuitry is configured and arranged to filter the database or the system of computer networks by triggering a filter of scale-obtained data with Internet based data in response to the aggregated data matching trigger data indicating the user is at risk for the health condition.

13. The apparatus of claim 11, further including the external circuitry configured and arranged to modify the weighing scale with treatment instructions that indicate a current treatment plan of the user and from the healthcare professional.

14. The apparatus of claim 13, wherein the processing circuitry is further configured and arranged to store and use the treatment instructions to remind the user of various goals, dietary considerations, appointments, prescription and/or shot schedules.

15. The apparatus of claim 13, wherein the processing circuitry is configured and arranged to track changes in physiological status of the user over time and compliance with the treatment plan, and provide suggestions or recommendations to the user for improving their health.

16. The apparatus of claim 13, wherein the processing circuitry is further configured and arranged to:

track the scale-obtained data and with user data obtained by the one or more user device or medical devices over time, identify potential correlations in changes in physiological status with the treatment plan or other causes using the tracked data, and output the tracked data and potential correlations to external circuitry of the healthcare professional for review.

17. The apparatus of claim 16, wherein the external circuitry is configured and arranged to output revised treatment instructions to the scale in response to the tracked data and correlations.

18. An apparatus for use with a plurality of user devices, each the plurality of user devices including circuitry to collect and to communicate user data, the apparatus comprising:

a weighing scale including:

a platform in which a plurality of sensors are integrated and configured and arranged for engaging a user; and processing circuitry including a CPU and a memory circuit configured and arranged under the platform upon which the user stands, wherein at least some of the processing circuitry is electrically connected with the plurality of sensors under the platform and configured to collect physiological data from the user by:

authorizing communication by the weighing scale platform with the plurality of user devices and/or medical devices and, in response to the authorization, receive the user data from the plurality of user devices and/or medical devices;

aggregating scale-obtained data collected from the user with the user data from the plurality of user devices and/or medical devices; and providing the aggregated data to external circuitry accessible by a healthcare professional.

19. The apparatus of claim 18, wherein the processing circuitry is configured and arranged to authorize the communication and further includes validating authorization data received from one or more of the plurality of user devices and/or medical devices and provided the aggregated data to the external circuitry automatically and without user input.

20. The apparatus of claim 18, further including the external circuitry configured and arranged to:

filter a database or a system of computer networks with the aggregated data in response to the aggregated data matching trigger data indicating the user is at risk for a health condition; and provide the aggregated data and filtered data to external circuitry for access by the healthcare professional for review and for providing on-demand care.

21. The apparatus of claim 18, wherein the processing circuitry is further configured and arranged to secure the aggregated data using one or more of an encryption scheme, software key, and hardware key, and communicates the secured aggregated data to the external circuitry using a secure communication connection.

\* \* \* \* \*